US012672872B2

(12) United States Patent (10) Patent No.: US 12,672,872 B2
Liu (45) Date of Patent: Jul. 7, 2026

(54) SURGICAL STAPLING DEVICE WITH SAFETY MEMBER

(71) Applicant: Covidien LP, Mansfield, MA (US)

(72) Inventor: Chirong Liu, Shanghai (CN)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/025,533

(22) PCT Filed: Sep. 30, 2020

(86) PCT No.: PCT/CN2020/119183
§ 371 (c)(1),
(2) Date: Mar. 9, 2023

(87) PCT Pub. No.: WO2022/067610
PCT Pub. Date: Apr. 7, 2022

(65) Prior Publication Data
US 2023/0329709 A1 Oct. 19, 2023

(51) Int. Cl.
*A61B 17/072* (2006.01)
*A61B 90/00* (2016.01)

(52) U.S. Cl.
CPC .................. *A61B 17/07207* (2013.01); *A61B 2017/07257* (2013.01); *A61B 2017/07271* (2013.01);
(Continued)

(58) Field of Classification Search
CPC ............ A61B 17/072; A61B 17/07207; A61B 17/2833; A61B 2017/07257;
(Continued)

(56) References Cited

U.S. PATENT DOCUMENTS 3,499,591 A 3/1970 Green
3,777,538 A 12/1973 Weatherly et al.
(Continued)

FOREIGN PATENT DOCUMENTS

AU 198654765 9/1986
CA 2773414 A1 11/2012
(Continued)

OTHER PUBLICATIONS

International Search Report and Written Opinion dated Jun. 21, 2021, issued in corresponding international application No. PCT/CN2020/119183, 9 pages.
(Continued)

*Primary Examiner* — Linda J. Hodge

(57) ABSTRACT

A safety member (100) for use with an open, linear stapling device (10) includes a body (102) that can be received within a central knife slot (72) of a staple cartridge (18) and includes a knife stop (104), an angled stop surface (106), and transverse protrusions (108). The knife stop (104) is positioned on the body (102) to engage a knife assembly (50) of the staple cartridge (18), and the angled stop surface (106) is positioned to engage an actuation sled (62) of the staple cartridge (18). The transverse protrusions (108) are positioned to be received within cutouts (110) of the staple cartridge (18) to prevent longitudinal movement of the safety member (100) in relation to the staple cartridge (18) when the safety member (100) is coupled to the staple cartridge (18).

19 Claims, 6 Drawing Sheets

(52) U.S. Cl.
CPC .............. *A61B 2017/07278* (2013.01); *A61B 2017/07285* (2013.01); *A61B 2090/034* (2016.02); *A61B 2090/08021* (2016.02)

(58) Field of Classification Search
CPC ........... A61B 2017/07271; A61B 2017/07285; A61B 2017/07278; A61B 2017/2829; A61B 2050/005; A61B 2090/034; A61B 2090/0801
USPC ................................ 227/175.2, 175.3–182.1
See application file for complete search history.

(56) References Cited

U.S. PATENT DOCUMENTS

| | | | |
|---|---|---|---|
| 3,882,854 A | 5/1975 | Hulka et al. |
| 4,027,510 A | 6/1977 | Hiltebrandt |
| 4,086,926 A | 5/1978 | Green et al. |
| 4,241,861 A | 12/1980 | Fleischer |
| 4,244,372 A | 1/1981 | Kapitanov et al. |
| 4,429,695 A | 2/1984 | Green |
| 4,505,414 A | 3/1985 | Filipi |
| 4,520,817 A | 6/1985 | Green |
| 4,589,413 A | 5/1986 | Malyshev et al. |
| 4,596,351 A | 6/1986 | Fedotov et al. |
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |

(56)                 References Cited

U.S. PATENT DOCUMENTS

| | | | |
|---|---|---|---|
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,690,675 A | 11/1997 | Sawyer et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Di et al. |
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milliman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,478,804 B2 | 11/2002 | Vargas et al. |
| 6,488,196 B1 | 12/2002 | Fenton, Jr. |

(56) References Cited

U.S. PATENT DOCUMENTS

| | | | |
|---|---|---|---|
| 6,503,257 B2 | 1/2003 | Grant et al. | |
| 6,505,768 B2 | 1/2003 | Whitman | |
| 6,544,274 B2 | 4/2003 | Danitz et al. | |
| 6,554,844 B2 | 4/2003 | Lee et al. | |
| 6,565,554 B1 | 5/2003 | Niemeyer | |
| 6,585,144 B2 * | 7/2003 | Adams | A61B 17/072 |
| | | | 227/19 |
| 6,587,750 B2 | 7/2003 | Gerbi et al. | |
| 6,592,597 B2 | 7/2003 | Grant et al. | |
| 6,594,552 B1 | 7/2003 | Nowlin et al. | |
| 6,602,252 B2 | 8/2003 | Mollenauer | |
| 6,619,529 B2 | 9/2003 | Green et al. | |
| D480,808 S | 10/2003 | Wells et al. | |
| 6,644,532 B2 | 11/2003 | Green et al. | |
| 6,656,193 B2 | 12/2003 | Grant et al. | |
| 6,669,073 B2 | 12/2003 | Milliman et al. | |
| 6,681,978 B2 | 1/2004 | Geiste et al. | |
| 6,698,643 B2 | 3/2004 | Whitman | |
| 6,716,232 B1 | 4/2004 | Vidal et al. | |
| 6,722,552 B2 | 4/2004 | Fenton, Jr. | |
| 6,755,338 B2 | 6/2004 | Hahnen et al. | |
| 6,783,524 B2 | 8/2004 | Anderson et al. | |
| 6,786,382 B1 | 9/2004 | Hoffman | |
| 6,817,509 B2 | 11/2004 | Geiste et al. | |
| 6,830,174 B2 | 12/2004 | Hillstead et al. | |
| 6,835,199 B2 | 12/2004 | McGuckin, Jr. et al. | |
| 6,843,403 B2 | 1/2005 | Whitman | |
| RE38,708 E | 3/2005 | Bolanos et al. | |
| 6,877,647 B2 | 4/2005 | Green et al. | |
| 6,889,116 B2 | 5/2005 | Jinno | |
| 6,905,057 B2 | 6/2005 | Swayze et al. | |
| 6,945,444 B2 | 9/2005 | Gresham et al. | |
| 6,953,138 B1 | 10/2005 | Dworak et al. | |
| 6,953,139 B2 | 10/2005 | Milliman et al. | |
| 6,959,852 B2 | 11/2005 | Shelton, IV et al. | |
| 6,962,594 B1 | 11/2005 | Thevenet | |
| 6,964,363 B2 | 11/2005 | Wales et al. | |
| 6,978,921 B2 | 12/2005 | Shelton, IV et al. | |
| 6,981,628 B2 | 1/2006 | Wales | |
| 6,986,451 B1 | 1/2006 | Mastri et al. | |
| 6,988,649 B2 | 1/2006 | Shelton, IV et al. | |
| 6,991,627 B2 | 1/2006 | Madhani et al. | |
| 6,994,714 B2 | 2/2006 | Vargas et al. | |
| 7,000,818 B2 | 2/2006 | Shelton, IV et al. | |
| 7,000,819 B2 | 2/2006 | Swayze et al. | |
| 7,032,799 B2 | 4/2006 | Viola et al. | |
| 7,044,352 B2 | 5/2006 | Shelton, IV et al. | |
| 7,044,353 B2 | 5/2006 | Mastri et al. | |
| 7,055,730 B2 | 6/2006 | Ehrenfels et al. | |
| 7,055,731 B2 | 6/2006 | Shelton, IV et al. | |
| 7,059,508 B2 | 6/2006 | Shelton, IV et al. | |
| 7,070,083 B2 | 7/2006 | Jankowski | |
| 7,083,075 B2 | 8/2006 | Swayze et al. | |
| 7,097,089 B2 | 8/2006 | Marczyk | |
| 7,111,769 B2 | 9/2006 | Wales et al. | |
| 7,114,642 B2 | 10/2006 | Whitman | |
| 7,121,446 B2 | 10/2006 | Arad et al. | |
| 7,128,253 B2 | 10/2006 | Mastri et al. | |
| 7,128,254 B2 | 10/2006 | Shelton, IV et al. | |
| 7,140,527 B2 | 11/2006 | Ehrenfels et al. | |
| 7,140,528 B2 | 11/2006 | Shelton, IV | |
| 7,143,923 B2 | 12/2006 | Shelton, IV et al. | |
| 7,143,924 B2 | 12/2006 | Scirica et al. | |
| 7,143,925 B2 | 12/2006 | Shelton, IV et al. | |
| 7,143,926 B2 | 12/2006 | Shelton, IV et al. | |
| 7,147,138 B2 | 12/2006 | Shelton, IV | |
| 7,159,750 B2 | 1/2007 | Racenet et al. | |
| 7,168,604 B2 | 1/2007 | Milliman et al. | |
| 7,172,104 B2 | 2/2007 | Scirica et al. | |
| 7,188,758 B2 | 3/2007 | Viola et al. | |
| 7,207,471 B2 | 4/2007 | Heinrich et al. | |
| 7,213,736 B2 | 5/2007 | Wales et al. | |
| 7,225,963 B2 | 6/2007 | Scirica | |
| 7,225,964 B2 | 6/2007 | Mastri et al. | |
| 7,238,195 B2 | 7/2007 | Viola | |
| 7,246,734 B2 | 7/2007 | Shelton, IV | |
| 7,258,262 B2 | 8/2007 | Mastri et al. | |
| 7,267,682 B1 | 9/2007 | Bender et al. | |
| 7,278,562 B2 | 10/2007 | Mastri et al. | |
| 7,278,563 B1 | 10/2007 | Green | |
| 7,287,682 B1 | 10/2007 | Ezzat et al. | |
| 7,293,685 B2 | 11/2007 | Ehrenfels et al. | |
| 7,296,722 B2 | 11/2007 | Ivanko | |
| 7,296,724 B2 | 11/2007 | Green et al. | |
| 7,296,772 B2 | 11/2007 | Wang | |
| 7,300,444 B1 | 11/2007 | Nielsen et al. | |
| 7,303,107 B2 | 12/2007 | Milliman et al. | |
| 7,303,108 B2 | 12/2007 | Shelton, IV | |
| 7,308,998 B2 | 12/2007 | Mastri et al. | |
| 7,326,232 B2 | 2/2008 | Viola et al. | |
| 7,328,828 B2 | 2/2008 | Ortiz et al. | |
| 7,328,829 B2 | 2/2008 | Arad et al. | |
| 7,334,717 B2 | 2/2008 | Rethy et al. | |
| 7,354,447 B2 | 4/2008 | Shelton, IV et al. | |
| 7,357,287 B2 | 4/2008 | Shelton, IV et al. | |
| 7,364,061 B2 | 4/2008 | Swayze et al. | |
| 7,367,485 B2 | 5/2008 | Shelton, IV et al. | |
| 7,377,928 B2 | 5/2008 | Zubik et al. | |
| 7,380,695 B2 | 6/2008 | Doll et al. | |
| 7,380,696 B2 | 6/2008 | Shelton, IV et al. | |
| 7,396,356 B2 | 7/2008 | Mollenauer | |
| 7,398,907 B2 | 7/2008 | Racenet et al. | |
| 7,399,310 B2 | 7/2008 | Edoga et al. | |
| 7,401,720 B1 | 7/2008 | Durrani | |
| 7,401,721 B2 | 7/2008 | Holsten et al. | |
| 7,404,508 B2 | 7/2008 | Smith et al. | |
| 7,404,509 B2 | 7/2008 | Ortiz et al. | |
| 7,407,074 B2 | 8/2008 | Ortiz et al. | |
| 7,407,075 B2 | 8/2008 | Holsten et al. | |
| 7,407,077 B2 | 8/2008 | Ortiz et al. | |
| 7,407,078 B2 | 8/2008 | Shelton, IV et al. | |
| 7,416,101 B2 | 8/2008 | Shelton, IV et al. | |
| 7,419,080 B2 | 9/2008 | Smith et al. | |
| 7,419,081 B2 | 9/2008 | Ehrenfels et al. | |
| 7,419,495 B2 | 9/2008 | Menn et al. | |
| 7,422,139 B2 | 9/2008 | Shelton, IV et al. | |
| 7,424,965 B2 | 9/2008 | Racenet et al. | |
| 7,431,189 B2 | 10/2008 | Shelton, IV et al. | |
| 7,431,730 B2 | 10/2008 | Viola | |
| 7,434,715 B2 | 10/2008 | Shelton, IV et al. | |
| 7,434,717 B2 | 10/2008 | Shelton, IV et al. | |
| 7,438,208 B2 | 10/2008 | Larson | |
| 7,438,209 B1 | 10/2008 | Hess et al. | |
| 7,441,684 B2 | 10/2008 | Shelton, IV et al. | |
| 7,441,685 B1 | 10/2008 | Boudreaux | |
| 7,448,525 B2 | 11/2008 | Shelton, IV et al. | |
| 7,451,904 B2 | 11/2008 | Shelton, IV | |
| 7,455,208 B2 | 11/2008 | Wales et al. | |
| 7,455,676 B2 | 11/2008 | Holsten et al. | |
| 7,458,494 B2 | 12/2008 | Matsutani et al. | |
| 7,461,767 B2 | 12/2008 | Viola et al. | |
| 7,462,185 B1 | 12/2008 | Knodel | |
| 7,464,846 B2 | 12/2008 | Shelton, IV et al. | |
| 7,464,847 B2 | 12/2008 | Viola et al. | |
| 7,464,848 B2 | 12/2008 | Green et al. | |
| 7,464,849 B2 | 12/2008 | Shelton, IV et al. | |
| 7,467,740 B2 | 12/2008 | Shelton, IV et al. | |
| 7,472,814 B2 | 1/2009 | Mastri et al. | |
| 7,472,815 B2 | 1/2009 | Shelton, IV et al. | |
| 7,472,816 B2 | 1/2009 | Holsten et al. | |
| 7,473,258 B2 | 1/2009 | Clauson et al. | |
| 7,481,347 B2 | 1/2009 | Roy | |
| 7,481,348 B2 | 1/2009 | Marczyk | |
| 7,481,349 B2 | 1/2009 | Holsten et al. | |
| 7,481,824 B2 | 1/2009 | Boudreaux et al. | |
| 7,487,899 B2 | 2/2009 | Shelton, IV et al. | |
| 7,490,749 B2 | 2/2009 | Schall et al. | |
| 7,494,039 B2 | 2/2009 | Racenet et al. | |
| 7,500,979 B2 | 3/2009 | Hueil et al. | |
| 7,503,474 B2 | 3/2009 | Hillstead et al. | |
| 7,506,790 B2 | 3/2009 | Shelton, IV | |
| 7,506,791 B2 | 3/2009 | Omaits et al. | |
| 7,510,107 B2 | 3/2009 | Timm et al. | |
| 7,513,408 B2 | 4/2009 | Shelton, IV et al. | |

(56)                    References Cited

U.S. PATENT DOCUMENTS

| | | | |
|---|---|---|---|
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,896 B2 | 10/2010 | Racenet |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,630 B2 | 11/2010 | Damadian et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Scirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |

(56)                References Cited

U.S. PATENT DOCUMENTS

| 7,913,893 | B2 | 3/2011 | Mastri et al. |
| 7,914,543 | B2 | 3/2011 | Roth et al. |
| 7,918,230 | B2 | 4/2011 | Whitman et al. |
| 7,922,061 | B2 | 4/2011 | Shelton, IV et al. |
| 7,922,063 | B2 | 4/2011 | Zemlok et al. |
| 7,922,064 | B2 | 4/2011 | Boyden et al. |
| 7,926,691 | B2 | 4/2011 | Viola et al. |
| 7,926,692 | B2 | 4/2011 | Racenet et al. |
| 7,934,628 | B2 | 5/2011 | Wenchell et al. |
| 7,934,630 | B2 | 5/2011 | Shelton, IV et al. |
| 7,934,631 | B2 | 5/2011 | Balbierz et al. |
| 7,942,300 | B2 | 5/2011 | Rethy et al. |
| 7,942,303 | B2 | 5/2011 | Shah |
| 7,950,560 | B2 | 5/2011 | Zemlok et al. |
| 7,950,561 | B2 | 5/2011 | Aranyi |
| 7,950,562 | B2 | 5/2011 | Beardsley et al. |
| 7,954,682 | B2 | 6/2011 | Giordano et al. |
| 7,954,683 | B1 | 6/2011 | Knodel et al. |
| 7,954,684 | B2 | 6/2011 | Boudreaux |
| 7,954,685 | B2 | 6/2011 | Viola |
| 7,954,686 | B2 | 6/2011 | Baxter, III et al. |
| 7,954,687 | B2 | 6/2011 | Zemlok et al. |
| 7,959,051 | B2 | 6/2011 | Smith et al. |
| 7,963,431 | B2 | 6/2011 | Scirica |
| 7,963,432 | B2 | 6/2011 | Knodel et al. |
| 7,963,433 | B2 | 6/2011 | Whitman et al. |
| 7,967,178 | B2 | 6/2011 | Scirica et al. |
| 7,967,179 | B2 | 6/2011 | Olson et al. |
| 7,967,180 | B2 | 6/2011 | Scirica |
| 7,975,894 | B2 | 7/2011 | Boyden et al. |
| 7,980,443 | B2 | 7/2011 | Scheib et al. |
| 7,988,026 | B2 | 8/2011 | Knodel et al. |
| 7,988,027 | B2 | 8/2011 | Olson et al. |
| 7,988,028 | B2 | 8/2011 | Farascioni et al. |
| 7,992,758 | B2 | 8/2011 | Whitman et al. |
| 7,997,468 | B2 | 8/2011 | Farascioni |
| 7,997,469 | B2 | 8/2011 | Olson et al. |
| 8,002,795 | B2 | 8/2011 | Beetel |
| 8,006,885 | B2 | 8/2011 | Marczyk |
| 8,006,887 | B2 | 8/2011 | Marczyk |
| 8,007,505 | B2 | 8/2011 | Weller et al. |
| 8,007,513 | B2 | 8/2011 | Nalagatla et al. |
| 8,011,550 | B2 | 9/2011 | Aranyi et al. |
| 8,011,551 | B2 | 9/2011 | Marczyk et al. |
| 8,011,552 | B2 | 9/2011 | Ivanko |
| 8,011,553 | B2 | 9/2011 | Mastri et al. |
| 8,011,555 | B2 | 9/2011 | Tarinelli et al. |
| 8,012,170 | B2 | 9/2011 | Whitman et al. |
| 8,015,976 | B2 | 9/2011 | Shah |
| 8,016,177 | B2 | 9/2011 | Bettuchi et al. |
| 8,016,178 | B2 | 9/2011 | Olson et al. |
| 8,020,742 | B2 | 9/2011 | Marczyk |
| 8,020,743 | B2 | 9/2011 | Shelton, IV |
| 8,028,882 | B2 | 10/2011 | Viola |
| 8,028,883 | B2 | 10/2011 | Stopek |
| 8,028,884 | B2 | 10/2011 | Sniffin et al. |
| 8,033,438 | B2 | 10/2011 | Scirica |
| 8,033,440 | B2 | 10/2011 | Wenchell et al. |
| 8,033,441 | B2 | 10/2011 | Marczyk |
| 8,033,442 | B2 | 10/2011 | Racenet et al. |
| 8,034,077 | B2 | 10/2011 | Smith et al. |
| 8,038,044 | B2 | 10/2011 | Viola |
| 8,038,045 | B2 | 10/2011 | Bettuchi et al. |
| 8,052,024 | B2 | 11/2011 | Viola et al. |
| 8,056,787 | B2 | 11/2011 | Boudreaux et al. |
| 8,056,788 | B2 | 11/2011 | Mastri et al. |
| 8,056,791 | B2 | 11/2011 | Whitman |
| 8,061,577 | B2 | 11/2011 | Racenet et al. |
| 8,066,166 | B2 | 11/2011 | Demmy et al. |
| 8,070,033 | B2 | 12/2011 | Milliman et al. |
| 8,070,034 | B1 | 12/2011 | Knodel |
| 8,070,035 | B2 | 12/2011 | Holsten et al. |
| 8,074,858 | B2 | 12/2011 | Marczyk |
| 8,074,859 | B2 | 12/2011 | Kostrzewski |
| 8,074,862 | B2 | 12/2011 | Shah |
| 8,083,118 | B2 | 12/2011 | Milliman et al. |
| 8,083,119 | B2 | 12/2011 | Prommersberger |
| 8,083,120 | B2 | 12/2011 | Shelton, IV et al. |
| 8,087,563 | B2 | 1/2012 | Milliman et al. |
| 8,091,753 | B2 | 1/2012 | Viola |
| 8,091,754 | B2 | 1/2012 | Ehrenfels et al. |
| 8,091,756 | B2 | 1/2012 | Viola |
| 8,092,493 | B2 | 1/2012 | Marczyk |
| 8,096,459 | B2 | 1/2012 | Ortiz et al. |
| 8,096,460 | B2 | 1/2012 | Blier et al. |
| 8,100,309 | B2 | 1/2012 | Marczyk |
| 8,100,310 | B2 | 1/2012 | Zemlok |
| 8,102,008 | B2 | 1/2012 | Wells |
| 8,113,405 | B2 | 2/2012 | Milliman |
| 8,113,406 | B2 | 2/2012 | Holsten et al. |
| 8,113,407 | B2 | 2/2012 | Holsten et al. |
| 8,113,408 | B2 | 2/2012 | Wenchell et al. |
| 8,113,409 | B2 | 2/2012 | Cohen et al. |
| 8,113,410 | B2 | 2/2012 | Hall et al. |
| 8,123,101 | B2 | 2/2012 | Racenet et al. |
| 8,127,975 | B2 | 3/2012 | Olson et al. |
| 8,127,976 | B2 | 3/2012 | Scirica et al. |
| 8,132,703 | B2 | 3/2012 | Milliman et al. |
| 8,132,705 | B2 | 3/2012 | Viola et al. |
| 8,132,706 | B2 | 3/2012 | Marczyk et al. |
| 8,136,713 | B2 | 3/2012 | Hathaway et al. |
| 8,141,762 | B2 | 3/2012 | Bedi et al. |
| 8,152,041 | B2 | 4/2012 | Kostrzewski |
| 8,157,148 | B2 | 4/2012 | Scirica |
| 8,157,150 | B2 | 4/2012 | Viola et al. |
| 8,157,151 | B2 | 4/2012 | Ingmanson et al. |
| 8,157,152 | B2 | 4/2012 | Holsten et al. |
| 8,162,197 | B2 | 4/2012 | Mastri et al. |
| 8,167,185 | B2 | 5/2012 | Shelton, IV et al. |
| 8,167,186 | B2 | 5/2012 | Racenet et al. |
| 8,172,121 | B2 | 5/2012 | Krehel |
| 8,172,124 | B2 | 5/2012 | Shelton, IV et al. |
| 8,181,837 | B2 | 5/2012 | Roy |
| 8,186,555 | B2 | 5/2012 | Shelton, IV et al. |
| 8,186,557 | B2 | 5/2012 | Cohen et al. |
| 8,186,558 | B2 | 5/2012 | Sapienza |
| 8,186,559 | B1 | 5/2012 | Whitman |
| 8,186,560 | B2 | 5/2012 | Hess et al. |
| 8,193,044 | B2 | 6/2012 | Kenneth |
| 8,196,795 | B2 | 6/2012 | Moore et al. |
| 8,196,796 | B2 | 6/2012 | Shelton, IV et al. |
| 8,201,721 | B2 | 6/2012 | Zemlok et al. |
| 8,205,619 | B2 | 6/2012 | Shah et al. |
| 8,205,780 | B2 | 6/2012 | Sorrentino et al. |
| 8,205,781 | B2 | 6/2012 | Baxter, III et al. |
| 8,210,412 | B2 | 7/2012 | Marczyk |
| 8,210,416 | B2 | 7/2012 | Milliman et al. |
| 8,215,532 | B2 | 7/2012 | Marczyk |
| 8,216,236 | B2 | 7/2012 | Heinrich et al. |
| 8,220,688 | B2 | 7/2012 | Laurent et al. |
| 8,220,690 | B2 | 7/2012 | Hess et al. |
| 8,225,979 | B2 | 7/2012 | Farascioni et al. |
| 8,231,040 | B2 | 7/2012 | Zemlok et al. |
| 8,231,041 | B2 | 7/2012 | Marczyk et al. |
| 8,235,272 | B2 | 8/2012 | Nicholas et al. |
| 8,235,273 | B2 | 8/2012 | Olson et al. |
| 8,235,274 | B2 | 8/2012 | Cappola |
| 8,236,010 | B2 | 8/2012 | Ortiz et al. |
| 8,240,536 | B2 | 8/2012 | Marczyk |
| 8,240,537 | B2 | 8/2012 | Marczyk |
| 8,241,322 | B2 | 8/2012 | Whitman et al. |
| 8,245,897 | B2 | 8/2012 | Tzakis et al. |
| 8,245,898 | B2 | 8/2012 | Smith et al. |
| 8,245,899 | B2 | 8/2012 | Swensgard et al. |
| 8,245,931 | B2 | 8/2012 | Shigeta |
| 8,252,009 | B2 | 8/2012 | Weller et al. |
| 8,256,653 | B2 | 9/2012 | Farascioni |
| 8,256,654 | B2 | 9/2012 | Bettuchi et al. |
| 8,256,655 | B2 | 9/2012 | Sniffin et al. |
| 8,256,656 | B2 | 9/2012 | Milliman et al. |
| 8,267,300 | B2 | 9/2012 | Boudreaux |
| 8,272,551 | B2 | 9/2012 | Knodel et al. |
| 8,272,553 | B2 | 9/2012 | Mastri et al. |
| 8,272,554 | B2 | 9/2012 | Whitman et al. |

(56) References Cited

U.S. PATENT DOCUMENTS

| | | | |
|---|---|---|---|
| 8,276,594 B2 | 10/2012 | Shah | |
| 8,276,801 B2 | 10/2012 | Zemlok et al. | |
| 8,281,973 B2 | 10/2012 | Wenchell et al. | |
| 8,286,847 B2 | 10/2012 | Taylor | |
| 8,286,848 B2 | 10/2012 | Wenchell et al. | |
| 8,286,850 B2 | 10/2012 | Viola | |
| 8,292,146 B2 | 10/2012 | Holsten et al. | |
| 8,292,147 B2 | 10/2012 | Viola | |
| 8,292,148 B2 | 10/2012 | Viola | |
| 8,292,149 B2 | 10/2012 | Ivanko | |
| 8,292,150 B2 | 10/2012 | Bryant | |
| 8,292,151 B2 | 10/2012 | Viola | |
| 8,292,152 B2 | 10/2012 | Milliman et al. | |
| 8,292,153 B2 | 10/2012 | Jankowski | |
| 8,292,154 B2 | 10/2012 | Marczyk | |
| 8,292,155 B2 | 10/2012 | Shelton, IV et al. | |
| 8,292,156 B2 | 10/2012 | Kostrzewski | |
| 8,292,158 B2 | 10/2012 | Sapienza | |
| 8,308,040 B2 | 11/2012 | Huang et al. | |
| 8,308,041 B2 | 11/2012 | Kostrzewski | |
| 8,308,042 B2 | 11/2012 | Aranyi | |
| 8,308,043 B2 | 11/2012 | Bindra et al. | |
| 8,308,044 B2 | 11/2012 | Viola | |
| 8,308,046 B2 | 11/2012 | Prommersberger | |
| 8,308,757 B2 | 11/2012 | Hillstead et al. | |
| 8,317,070 B2 | 11/2012 | Hueil et al. | |
| 8,317,071 B1 | 11/2012 | Knodel | |
| 8,322,455 B2 | 12/2012 | Shelton, IV et al. | |
| 8,322,589 B2 | 12/2012 | Boudreaux | |
| 8,328,061 B2 | 12/2012 | Kasvikis | |
| 8,328,065 B2 | 12/2012 | Shah | |
| 8,333,313 B2 | 12/2012 | Boudreaux et al. | |
| 8,336,751 B2 | 12/2012 | Scirica | |
| 8,336,753 B2 | 12/2012 | Olson et al. | |
| 8,336,754 B2 | 12/2012 | Cappola et al. | |
| 8,342,377 B2 | 1/2013 | Milliman et al. | |
| 8,342,378 B2 | 1/2013 | Marczyk et al. | |
| 8,342,379 B2 | 1/2013 | Whitman et al. | |
| 8,342,380 B2 | 1/2013 | Viola | |
| 8,348,123 B2 | 1/2013 | Scirica et al. | |
| 8,348,124 B2 | 1/2013 | Scirica | |
| 8,348,125 B2 | 1/2013 | Viola et al. | |
| 8,348,126 B2 | 1/2013 | Olson et al. | |
| 8,348,127 B2 | 1/2013 | Marczyk | |
| 8,348,129 B2 | 1/2013 | Bedi et al. | |
| 8,348,130 B2 | 1/2013 | Shah et al. | |
| 8,348,131 B2 | 1/2013 | Omaits et al. | |
| 8,353,437 B2 | 1/2013 | Boudreaux | |
| 8,353,440 B2 | 1/2013 | Whitman et al. | |
| 8,356,740 B1 | 1/2013 | Knodel | |
| 8,357,174 B2 | 1/2013 | Roth et al. | |
| 8,360,294 B2 | 1/2013 | Scirica | |
| 8,360,297 B2 | 1/2013 | Shelton, IV et al. | |
| 8,360,298 B2 | 1/2013 | Farascioni et al. | |
| 8,360,299 B2 | 1/2013 | Zemlok et al. | |
| 8,365,971 B1 | 2/2013 | Knodel | |
| 8,365,972 B2 | 2/2013 | Aranyi et al. | |
| 8,365,973 B1 | 2/2013 | White et al. | |
| 8,365,976 B2 | 2/2013 | Hess et al. | |
| 8,371,491 B2 | 2/2013 | Huitema et al. | |
| 8,371,492 B2 | 2/2013 | Aranyi et al. | |
| 8,371,493 B2 | 2/2013 | Aranyi et al. | |
| 8,381,828 B2 | 2/2013 | Whitman et al. | |
| 8,381,961 B2 | 2/2013 | Holsten et al. | |
| 8,387,848 B2 | 3/2013 | Johnson et al. | |
| 8,387,849 B2 | 3/2013 | Buesseler et al. | |
| 8,387,850 B2 | 3/2013 | Hathaway et al. | |
| 8,388,652 B2 | 3/2013 | Viola | |
| 8,393,513 B2 | 3/2013 | Jankowski | |
| 8,393,514 B2 | 3/2013 | Shelton, IV et al. | |
| 8,393,516 B2 | 3/2013 | Kostrzewski | |
| 8,397,971 B2 | 3/2013 | Yates et al. | |
| 8,397,972 B2 | 3/2013 | Kostrzewski | |
| 8,403,195 B2 | 3/2013 | Beardsley et al. | |
| 8,403,196 B2 | 3/2013 | Beardsley et al. | |
| 8,403,197 B2 | 3/2013 | Vidal et al. | |
| 8,403,198 B2 | 3/2013 | Sorrentino et al. | |
| 8,403,956 B1 | 3/2013 | Thompson et al. | |
| 8,408,439 B2 | 4/2013 | Huang et al. | |
| 8,408,440 B2 | 4/2013 | Olson et al. | |
| 8,408,442 B2 | 4/2013 | Racenet et al. | |
| 8,413,868 B2 | 4/2013 | Cappola | |
| 8,413,869 B2 | 4/2013 | Heinrich | |
| 8,413,871 B2 | 4/2013 | Racenet et al. | |
| 8,418,904 B2 | 4/2013 | Wenchell et al. | |
| 8,418,905 B2 | 4/2013 | Milliman | |
| 8,418,906 B2 | 4/2013 | Farascioni et al. | |
| 8,418,907 B2 | 4/2013 | Johnson et al. | |
| 8,418,908 B1 | 4/2013 | Beardsley | |
| 8,419,768 B2 | 4/2013 | Marczyk | |
| 8,424,735 B2 | 4/2013 | Viola et al. | |
| 8,424,736 B2 | 4/2013 | Scirica et al. | |
| 8,424,737 B2 | 4/2013 | Scirica | |
| 8,424,739 B2 | 4/2013 | Racenet et al. | |
| 8,424,740 B2 | 4/2013 | Shelton, IV et al. | |
| 8,439,244 B2 | 5/2013 | Holcomb et al. | |
| 8,439,245 B2 | 5/2013 | Knodel et al. | |
| 8,439,246 B1 | 5/2013 | Knodel | |
| 8,444,036 B2 | 5/2013 | Shelton, IV | |
| 8,444,037 B2 | 5/2013 | Nicholas et al. | |
| 8,444,038 B2 | 5/2013 | Farascioni et al. | |
| 8,448,832 B2 | 5/2013 | Viola et al. | |
| 8,453,652 B2 | 6/2013 | Stopek | |
| 8,453,905 B2 | 6/2013 | Holcomb et al. | |
| 8,453,906 B2 | 6/2013 | Huang et al. | |
| 8,453,907 B2 | 6/2013 | Laurent et al. | |
| 8,453,908 B2 | 6/2013 | Bedi et al. | |
| 8,453,909 B2 | 6/2013 | Olson et al. | |
| 8,453,910 B2 | 6/2013 | Bettuchi et al. | |
| 8,453,912 B2 | 6/2013 | Mastri et al. | |
| 8,453,913 B2 | 6/2013 | Milliman | |
| 8,453,914 B2 | 6/2013 | Laurent et al. | |
| 8,454,628 B2 | 6/2013 | Smith et al. | |
| 8,459,520 B2 | 6/2013 | Giordano et al. | |
| 8,459,521 B2 | 6/2013 | Zemlok et al. | |
| 8,459,522 B2 | 6/2013 | Marczyk | |
| 8,459,523 B2 | 6/2013 | Whitman | |
| 8,459,524 B2 | 6/2013 | Pribanic et al. | |
| 8,459,525 B2 | 6/2013 | Yates et al. | |
| 8,464,922 B2 | 6/2013 | Marczyk | |
| 8,464,923 B2 | 6/2013 | Shelton, IV | |
| 8,469,252 B2 | 6/2013 | Holcomb et al. | |
| 8,469,254 B2 | 6/2013 | Czernik et al. | |
| 8,474,677 B2 | 7/2013 | Woodard, Jr. et al. | |
| 8,479,967 B2 | 7/2013 | Marczyk | |
| 8,479,968 B2 | 7/2013 | Hodgkinson et al. | |
| 8,479,969 B2 | 7/2013 | Shelton, IV | |
| 8,485,412 B2 | 7/2013 | Shelton, IV et al. | |
| 8,490,852 B2 | 7/2013 | Viola | |
| 8,496,152 B2 | 7/2013 | Viola | |
| 8,496,154 B2 | 7/2013 | Marczyk et al. | |
| 8,496,156 B2 | 7/2013 | Sniffin et al. | |
| 8,496,683 B2 | 7/2013 | Prommersberger et al. | |
| 8,499,993 B2 | 8/2013 | Shelton, IV et al. | |
| 8,505,799 B2 | 8/2013 | Viola et al. | |
| 8,505,802 B2 | 8/2013 | Viola et al. | |
| 8,511,575 B2 | 8/2013 | Kok | |
| 8,512,359 B2 | 8/2013 | Whitman et al. | |
| 8,512,402 B2 | 8/2013 | Marczyk et al. | |
| 8,517,240 B1 | 8/2013 | Mata et al. | |
| 8,517,241 B2 | 8/2013 | Nicholas et al. | |
| 8,517,243 B2 | 8/2013 | Giordano et al. | |
| 8,517,244 B2 | 8/2013 | Shelton, IV et al. | |
| 8,523,041 B2 | 9/2013 | Ishitsuki et al. | |
| 8,523,042 B2 | 9/2013 | Masiakos et al. | |
| 8,523,043 B2 | 9/2013 | Ullrich et al. | |
| 8,534,528 B2 | 9/2013 | Shelton, IV | |
| 8,540,128 B2 | 9/2013 | Shelton, IV et al. | |
| 8,540,129 B2 | 9/2013 | Baxter, III et al. | |
| 8,540,130 B2 | 9/2013 | Moore et al. | |
| 8,540,131 B2 | 9/2013 | Swayze | |
| 8,540,733 B2 | 9/2013 | Whitman et al. | |
| 8,544,711 B2 | 10/2013 | Ma et al. | |
| 8,550,325 B2 | 10/2013 | Cohen et al. | |

(56)             References Cited

U.S. PATENT DOCUMENTS

| | | | |
|---|---|---|---|
| 8,556,151 | B2 | 10/2013 | Viola |
| 8,561,870 | B2 | 10/2013 | Baxter, III et al. |
| 8,561,873 | B2 | 10/2013 | Ingmanson et al. |
| 8,561,874 | B2 | 10/2013 | Scirica |
| 8,567,656 | B2 | 10/2013 | Shelton, IV et al. |
| 8,573,461 | B2 | 11/2013 | Shelton, IV et al. |
| 8,573,463 | B2 | 11/2013 | Scirica et al. |
| 8,573,465 | B2 | 11/2013 | Shelton, IV |
| 8,579,176 | B2 | 11/2013 | Smith et al. |
| 8,579,177 | B2 | 11/2013 | Beetel |
| 8,584,919 | B2 | 11/2013 | Hueil et al. |
| 8,584,920 | B2 | 11/2013 | Hodgkinson |
| 8,590,762 | B2 | 11/2013 | Hess et al. |
| 8,596,515 | B2 | 12/2013 | Okoniewski |
| 8,597,311 | B2 | 12/2013 | Criscuolo et al. |
| 8,602,288 | B2 | 12/2013 | Shelton, IV et al. |
| 8,608,045 | B2 | 12/2013 | Smith et al. |
| 8,608,046 | B2 | 12/2013 | Laurent et al. |
| 8,608,047 | B2 | 12/2013 | Holsten et al. |
| 8,613,383 | B2 | 12/2013 | Beckman et al. |
| 8,613,384 | B2 | 12/2013 | Pastorelli et al. |
| 8,616,427 | B2 | 12/2013 | Viola |
| 8,616,430 | B2 | 12/2013 | Stopek et al. |
| 8,627,994 | B2 | 1/2014 | Zemlok et al. |
| 8,628,544 | B2 | 1/2014 | Farascioni |
| 8,631,988 | B2 | 1/2014 | Viola |
| 8,631,989 | B2 | 1/2014 | Aranyi et al. |
| 8,631,991 | B2 | 1/2014 | Cropper et al. |
| 8,632,525 | B2 | 1/2014 | Kerr et al. |
| 8,632,535 | B2 | 1/2014 | Shelton, IV et al. |
| 8,636,187 | B2 | 1/2014 | Hueil et al. |
| 8,636,190 | B2 | 1/2014 | Zemlok et al. |
| 8,636,192 | B2 | 1/2014 | Farascioni et al. |
| 8,636,762 | B2 | 1/2014 | Whitman et al. |
| 8,636,766 | B2 | 1/2014 | Milliman et al. |
| 8,640,940 | B2 | 2/2014 | Ohdaira |
| 8,657,174 | B2 | 2/2014 | Yates et al. |
| 8,657,177 | B2 | 2/2014 | Scirica et al. |
| 8,657,178 | B2 | 2/2014 | Hueil et al. |
| 8,662,371 | B2 | 3/2014 | Viola |
| 8,668,129 | B2 | 3/2014 | Olson |
| 8,672,206 | B2 | 3/2014 | Aranyi et al. |
| 8,672,208 | B2 | 3/2014 | Hess et al. |
| 8,672,209 | B2 | 3/2014 | Crainich |
| 8,678,263 | B2 | 3/2014 | Viola |
| 8,678,990 | B2 | 3/2014 | Wazer et al. |
| 8,679,155 | B2 | 3/2014 | Knodel et al. |
| 8,684,247 | B2 | 4/2014 | Scirica et al. |
| 8,684,249 | B2 | 4/2014 | Racenet et al. |
| 8,684,253 | B2 | 4/2014 | Giordano et al. |
| 8,690,039 | B2 | 4/2014 | Beardsley et al. |
| 8,695,865 | B2 | 4/2014 | Smith et al. |
| 8,695,866 | B2 | 4/2014 | Leimbach et al. |
| 8,701,958 | B2 | 4/2014 | Shelton, IV et al. |
| 8,701,959 | B2 | 4/2014 | Shah |
| 8,701,961 | B2 | 4/2014 | Ivanko |
| 8,708,213 | B2 | 4/2014 | Shelton, IV et al. |
| 8,714,429 | B2 | 5/2014 | Demmy |
| 8,715,277 | B2 | 5/2014 | Weizman |
| 8,720,766 | B2 | 5/2014 | Hess et al. |
| 8,721,630 | B2 | 5/2014 | Ortiz et al. |
| 8,727,197 | B2 | 5/2014 | Hess et al. |
| 8,727,200 | B2 | 5/2014 | Roy |
| 8,733,612 | B2 | 5/2014 | Ma |
| 8,740,034 | B2 | 6/2014 | Morgan et al. |
| 8,740,039 | B2 | 6/2014 | Farascioni |
| 8,746,529 | B2 | 6/2014 | Shelton, IV et al. |
| 8,746,530 | B2 | 6/2014 | Giordano et al. |
| 8,746,533 | B2 | 6/2014 | Whitman |
| 8,746,534 | B2 | 6/2014 | Farascioni |
| 8,746,535 | B2 | 6/2014 | Shelton, IV et al. |
| 8,747,421 | B2 | 6/2014 | Balbierz et al. |
| 8,752,747 | B2 | 6/2014 | Shelton, IV et al. |
| 8,752,748 | B2 | 6/2014 | Whitman et al. |
| 8,752,749 | B2 | 6/2014 | Moore et al. |
| 8,757,465 | B2 | 6/2014 | Woodard, Jr. et al. |
| 8,758,391 | B2 | 6/2014 | Swayze et al. |
| 8,763,875 | B2 | 7/2014 | Morgan et al. |
| 8,763,876 | B2 | 7/2014 | Kostrzewski |
| 8,763,877 | B2 | 7/2014 | Schall et al. |
| 8,763,879 | B2 | 7/2014 | Shelton, IV et al. |
| 8,770,458 | B2 | 7/2014 | Scirica |
| 8,777,082 | B2 | 7/2014 | Scirica |
| 8,783,541 | B2 | 7/2014 | Shelton, IV et al. |
| 8,783,542 | B2 | 7/2014 | Riestenberg et al. |
| 8,789,737 | B2 | 7/2014 | Hodgkinson et al. |
| 8,789,738 | B2 | 7/2014 | Knodel et al. |
| 8,789,739 | B2 | 7/2014 | Swensgard |
| 8,800,838 | B2 | 8/2014 | Shelton, IV |
| 8,800,840 | B2 | 8/2014 | Jankowski |
| 8,800,841 | B2 | 8/2014 | Ellerhorst et al. |
| 8,808,311 | B2 | 8/2014 | Heinrich et al. |
| 8,814,024 | B2 | 8/2014 | Woodard, Jr. et al. |
| 8,814,025 | B2 | 8/2014 | Miller et al. |
| 8,820,603 | B2 | 9/2014 | Shelton, IV et al. |
| 8,820,605 | B2 | 9/2014 | Shelton, IV |
| 8,820,606 | B2 | 9/2014 | Hodgkinson |
| 8,820,607 | B2 | 9/2014 | Marczyk |
| 8,827,133 | B2 | 9/2014 | Shelton, IV et al. |
| 8,827,134 | B2 | 9/2014 | Viola et al. |
| 8,833,631 | B2 | 9/2014 | Munro, III et al. |
| 8,833,632 | B2 | 9/2014 | Swensgard |
| 8,840,003 | B2 | 9/2014 | Morgan et al. |
| 8,840,603 | B2 | 9/2014 | Shelton, IV et al. |
| 8,844,788 | B2 | 9/2014 | Knodel |
| 8,851,354 | B2 | 10/2014 | Swensgard et al. |
| 8,851,355 | B2 | 10/2014 | Aranyi et al. |
| 8,857,693 | B2 | 10/2014 | Schuckmann et al. |
| 8,864,007 | B2 | 10/2014 | Widenhouse et al. |
| 8,864,009 | B2 | 10/2014 | Shelton, IV et al. |
| 8,864,010 | B2 | 10/2014 | Williams |
| 8,870,050 | B2 | 10/2014 | Hodgkinson |
| 8,875,971 | B2 | 11/2014 | Hall et al. |
| 8,875,972 | B2 | 11/2014 | Weisenburgh, II et al. |
| 8,893,949 | B2 | 11/2014 | Shelton, IV et al. |
| 8,893,950 | B2 | 11/2014 | Marczyk |
| 8,899,461 | B2 | 12/2014 | Farascioni |
| 8,899,462 | B2 | 12/2014 | Kostrzewski et al. |
| 8,899,463 | B2 | 12/2014 | Schall et al. |
| 8,899,464 | B2 | 12/2014 | Hueil et al. |
| 8,900,616 | B2 | 12/2014 | Belcheva et al. |
| 8,920,435 | B2 | 12/2014 | Smith et al. |
| 8,925,782 | B2 | 1/2015 | Shelton, IV |
| 8,926,598 | B2 | 1/2015 | Mollere et al. |
| 8,931,681 | B2 | 1/2015 | Kostrzewski |
| 8,931,682 | B2 | 1/2015 | Timm et al. |
| 8,931,693 | B1 | 1/2015 | Kumar et al. |
| 8,955,732 | B2 | 2/2015 | Zemlok et al. |
| 8,958,429 | B2 | 2/2015 | Shukla et al. |
| 8,960,517 | B2 | 2/2015 | Lee |
| 8,960,520 | B2 | 2/2015 | McCuen |
| 8,967,443 | B2 | 3/2015 | McCuen |
| 8,967,446 | B2 | 3/2015 | Beardsley et al. |
| 8,973,803 | B2 | 3/2015 | Hall et al. |
| 8,978,954 | B2 | 3/2015 | Shelton, IV et al. |
| 8,978,956 | B2 | 3/2015 | Schall et al. |
| 8,991,677 | B2 | 3/2015 | Moore et al. |
| 8,991,678 | B2 | 3/2015 | Wellman et al. |
| 8,998,058 | B2 | 4/2015 | Moore et al. |
| 8,998,060 | B2 | 4/2015 | Bruewer et al. |
| 9,005,230 | B2 | 4/2015 | Yates et al. |
| 9,010,606 | B2 | 4/2015 | Aranyi et al. |
| 9,010,607 | B2 | 4/2015 | Kostrzewski |
| 9,010,610 | B2 | 4/2015 | Hodgkinson |
| 9,016,539 | B2 | 4/2015 | Kostrzewski et al. |
| 9,016,541 | B2 | 4/2015 | Viola et al. |
| 9,016,542 | B2 | 4/2015 | Shelton, IV et al. |
| 9,016,544 | B2 | 4/2015 | Hodgkinson et al. |
| 9,016,545 | B2 | 4/2015 | Aranyi et al. |
| 9,016,546 | B2 | 4/2015 | Demmy et al. |
| 9,017,371 | B2 | 4/2015 | Whitman et al. |
| 9,022,271 | B2 | 5/2015 | Scirica |
| 9,027,817 | B2 | 5/2015 | Milliman et al. |
| 9,033,203 | B2 | 5/2015 | Woodard, Jr. et al. |

(56)          References Cited

U.S. PATENT DOCUMENTS

| | | | |
|---|---|---|---|
| 9,044,228 B2 | 6/2015 | Woodard, Jr. et al. |
| 9,044,229 B2 | 6/2015 | Scheib et al. |
| 9,050,084 B2 | 6/2015 | Schmid et al. |
| 9,055,941 B2 | 6/2015 | Schmid et al. |
| 9,060,770 B2 | 6/2015 | Shelton, IV et al. |
| 9,072,535 B2 | 7/2015 | Shelton, IV et al. |
| 9,084,601 B2 | 7/2015 | Moore et al. |
| 9,084,602 B2 | 7/2015 | Gleiman |
| 9,089,326 B2 | 7/2015 | Krumanaker et al. |
| 9,095,339 B2 | 8/2015 | Moore et al. |
| 9,101,359 B2 | 8/2015 | Smith et al. |
| 9,107,663 B2 | 8/2015 | Swensgard |
| 9,107,664 B2 | 8/2015 | Marczyk |
| 9,107,667 B2 | 8/2015 | Hodgkinson |
| 9,113,862 B2 | 8/2015 | Morgan et al. |
| 9,113,864 B2 | 8/2015 | Morgan et al. |
| 9,113,870 B2 | 8/2015 | Viola |
| 9,113,872 B2 | 8/2015 | Viola |
| 9,113,880 B2 | 8/2015 | Zemlok et al. |
| 9,125,649 B2 | 9/2015 | Bruewer et al. |
| 9,138,225 B2 | 9/2015 | Huang et al. |
| 9,155,537 B2 | 10/2015 | Katre et al. |
| 9,179,912 B2 | 11/2015 | Yates et al. |
| 9,192,378 B2 | 11/2015 | Aranyi et al. |
| 9,192,379 B2 | 11/2015 | Aranyi et al. |
| 9,192,384 B2 | 11/2015 | Bettuchi |
| 9,198,644 B2 | 12/2015 | Balek et al. |
| 9,198,660 B2 | 12/2015 | Hodgkinson |
| 9,198,661 B2 | 12/2015 | Swensgard |
| 9,198,662 B2 | 12/2015 | Barton et al. |
| 9,204,876 B2 | 12/2015 | Cappola et al. |
| 9,204,877 B2 | 12/2015 | Whitman et al. |
| 9,204,880 B2 | 12/2015 | Baxter, III et al. |
| 9,216,019 B2 | 12/2015 | Schmid et al. |
| 9,216,020 B2 | 12/2015 | Zhang et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,232,941 B2 | 1/2016 | Mandakolathur Vasudevan et al. |
| 9,232,944 B2 | 1/2016 | Cappola et al. |
| 9,237,891 B2 | 1/2016 | Shelton, IV |
| 9,237,892 B2 | 1/2016 | Hodgkinson |
| 9,254,180 B2 | 2/2016 | Huitema et al. |
| 9,265,585 B2 | 2/2016 | Wingardner et al. |
| 9,271,728 B2 | 3/2016 | Gupta et al. |
| 9,272,406 B2 | 3/2016 | Aronhalt et al. |
| 9,277,919 B2 | 3/2016 | Timmer et al. |
| 9,282,962 B2 | 3/2016 | Schmid et al. |
| 9,283,054 B2 | 3/2016 | Morgan et al. |
| 9,289,209 B2 | 3/2016 | Gurumurthy et al. |
| 9,289,210 B2 | 3/2016 | Baxter, III et al. |
| 9,289,225 B2 | 3/2016 | Shelton, IV et al. |
| 9,295,464 B2 | 3/2016 | Shelton, IV et al. |
| 9,295,465 B2 | 3/2016 | Farascioni |
| 9,295,466 B2 | 3/2016 | Hodgkinson et al. |
| 9,301,752 B2 | 4/2016 | Mandakolathur Vasudevan et al. |
| 9,301,753 B2 | 4/2016 | Aldridge et al. |
| 9,301,757 B2 | 4/2016 | Williams |
| 9,301,759 B2 | 4/2016 | Spivey et al. |
| 9,307,965 B2 | 4/2016 | Ming et al. |
| 9,307,986 B2 | 4/2016 | Hall et al. |
| 9,307,989 B2 | 4/2016 | Shelton, IV et al. |
| 9,314,246 B2 | 4/2016 | Shelton, IV et al. |
| 9,320,518 B2 | 4/2016 | Henderson et al. |
| 9,320,521 B2 | 4/2016 | Shelton, IV et al. |
| 9,320,523 B2 | 4/2016 | Shelton, IV et al. |
| 9,326,767 B2 | 5/2016 | Koch, Jr. et al. |
| 9,326,771 B2 | 5/2016 | Baxter, III et al. |
| 9,332,987 B2 | 5/2016 | Leimbach et al. |
| 9,345,477 B2 | 5/2016 | Anim et al. |
| 9,345,478 B2 | 5/2016 | Knodel |
| 9,345,479 B2 | 5/2016 | Racenet et al. |
| 9,345,481 B2 | 5/2016 | Hall et al. |
| 9,345,780 B2 | 5/2016 | Manoharan et al. |
| 9,351,726 B2 | 5/2016 | Leimbach |
| 9,351,727 B2 | 5/2016 | Leimbach et al. |
| 9,351,732 B2 | 5/2016 | Hodgkinson |
| 9,358,003 B2 | 6/2016 | Hall et al. |
| 9,364,217 B2 | 6/2016 | Kostrzewski et al. |
| 9,364,218 B2 | 6/2016 | Scirica |
| 9,364,219 B2 | 6/2016 | Olson et al. |
| 9,364,220 B2 | 6/2016 | Williams |
| 9,364,227 B2 | 6/2016 | Kostrzewski |
| 9,364,231 B2 | 6/2016 | Wenchell |
| 9,364,233 B2 | 6/2016 | Alexander, III et al. |
| 9,370,358 B2 | 6/2016 | Shelton, IV et al. |
| 9,370,362 B2 | 6/2016 | Petty et al. |
| 9,386,983 B2 | 7/2016 | Swensgard et al. |
| 9,386,984 B2 * | 7/2016 | Aronhalt ............ A61B 17/0682 |
| 9,386,988 B2 | 7/2016 | Baxter, III et al. |
| 9,393,018 B2 | 7/2016 | Wang et al. |
| 9,398,911 B2 | 7/2016 | Auld |
| 9,402,604 B2 | 8/2016 | Williams et al. |
| 9,402,627 B2 | 8/2016 | Stevenson et al. |
| 9,421,014 B2 | 8/2016 | Ingmanson et al. |
| 9,433,419 B2 | 9/2016 | Gonzalez et al. |
| 9,433,420 B2 | 9/2016 | Hodgkinson |
| 9,445,810 B2 | 9/2016 | Cappola |
| 9,445,813 B2 | 9/2016 | Shelton, IV et al. |
| 9,451,959 B2 | 9/2016 | Patankar et al. |
| 9,468,438 B2 | 10/2016 | Baber et al. |
| 9,468,439 B2 | 10/2016 | Cappola et al. |
| 9,480,476 B2 | 11/2016 | Aldridge et al. |
| 9,480,492 B2 | 11/2016 | Aranyi et al. |
| 9,492,171 B2 | 11/2016 | Patenaude |
| 9,498,212 B2 | 11/2016 | Racenet et al. |
| 9,498,219 B2 | 11/2016 | Moore et al. |
| 9,510,827 B2 | 12/2016 | Kostrzewski |
| 9,517,065 B2 | 12/2016 | Simms et al. |
| 9,517,066 B2 | 12/2016 | Racenet et al. |
| 9,522,002 B2 | 12/2016 | Chowaniec et al. |
| 9,539,007 B2 | 1/2017 | Dhakad et al. |
| 9,549,735 B2 | 1/2017 | Shelton, IV et al. |
| 9,554,794 B2 | 1/2017 | Baber |
| 9,561,029 B2 | 2/2017 | Scheib et al. |
| 9,561,031 B2 | 2/2017 | Heinrich et al. |
| 9,566,065 B2 | 2/2017 | Knodel |
| 9,572,576 B2 | 2/2017 | Hodgkinson et al. |
| 9,579,101 B2 | 2/2017 | Whitman et al. |
| 9,585,657 B2 | 3/2017 | Shelton, IV et al. |
| 9,585,662 B2 | 3/2017 | Shelton, IV et al. |
| 9,597,077 B2 | 3/2017 | Hodgkinson |
| 9,610,080 B2 | 4/2017 | Whitfield et al. |
| 9,615,825 B2 | 4/2017 | Viola |
| 9,615,826 B2 | 4/2017 | Shelton, IV et al. |
| 9,622,746 B2 | 4/2017 | Simms |
| 9,629,623 B2 | 4/2017 | Ytle, IV et al. |
| 9,629,626 B2 | 4/2017 | Soltz et al. |
| 9,629,628 B2 | 4/2017 | Aranyi |
| 9,629,629 B2 | 4/2017 | Leimbach et al. |
| 9,642,620 B2 | 5/2017 | Baxter, III |
| 9,649,109 B2 | 5/2017 | Ranucci et al. |
| 9,655,613 B2 | 5/2017 | Schaller |
| 9,662,108 B2 | 5/2017 | Williams |
| 9,668,728 B2 | 6/2017 | Williams et al. |
| 9,668,732 B2 | 6/2017 | Patel et al. |
| 9,675,351 B2 | 6/2017 | Hodgkinson et al. |
| 9,681,870 B2 | 6/2017 | Baxter, III et al. |
| 9,687,230 B2 | 6/2017 | Leimbach et al. |
| 9,687,233 B2 | 6/2017 | Fernandez et al. |
| 9,693,772 B2 | 7/2017 | Ingmanson et al. |
| 9,700,309 B2 | 7/2017 | Jaworek |
| 9,700,319 B2 | 7/2017 | Motooka et al. |
| 9,706,993 B2 | 7/2017 | Hessler et al. |
| 9,713,474 B2 | 7/2017 | Lorenz |
| 9,717,497 B2 | 8/2017 | Zerkle et al. |
| 9,717,498 B2 | 8/2017 | Aranyi et al. |
| 9,724,092 B2 | 8/2017 | Baxter, III et al. |
| 9,724,095 B2 | 8/2017 | Gupta et al. |
| 9,730,694 B2 * | 8/2017 | Scirica ............... A61B 17/0682 |
| 9,757,125 B2 * | 9/2017 | Wellman .......... A61B 17/07207 |
| 9,763,662 B2 | 9/2017 | Shelton, IV et al. |
| 9,770,245 B2 | 9/2017 | Swayze et al. |
| 9,775,610 B2 | 10/2017 | Nicholas et al. |

(56) References Cited

U.S. PATENT DOCUMENTS

| | | | |
|---|---|---|---|
| 9,775,635 B2 | 10/2017 | Takei |
| 9,782,169 B2 | 10/2017 | Kimsey |
| 9,782,173 B2 | 10/2017 | Mozdzierz |
| 9,795,379 B2 | 10/2017 | Leimbach et al. |
| 9,795,384 B2 | 10/2017 | Weaner et al. |
| 9,808,246 B2 | 11/2017 | Shelton, IV |
| 9,808,248 B2 | 11/2017 | Hoffman |
| 9,808,249 B2 | 11/2017 | Shelton, IV |
| 9,820,741 B2 | 11/2017 | Kostrzewski |
| 9,820,742 B2 | 11/2017 | Covach et al. |
| 9,827,002 B2 | 11/2017 | Hausen et al. |
| 9,839,420 B2 | 12/2017 | Shelton, IV |
| 9,839,421 B2 | 12/2017 | Zerkle et al. |
| 9,839,428 B2 | 12/2017 | Baxter et al. |
| 9,855,038 B2 | 1/2018 | Smith et al. |
| 9,855,040 B2 | 1/2018 | Kostrzewski |
| 9,861,358 B2 | 1/2018 | Marczyk et al. |
| 9,861,359 B2 | 1/2018 | Shelton, IV et al. |
| 9,867,612 B2 | 1/2018 | Parihar et al. |
| 9,867,613 B2 | 1/2018 | Marczyk et al. |
| 9,867,615 B2 | 1/2018 | Fanelli et al. |
| 9,872,683 B2 | 1/2018 | Hopkins |
| 9,883,860 B2 | 2/2018 | Leimbach et al. |
| 9,901,342 B2 | 2/2018 | Shelton, IV et al. |
| 9,913,646 B2 | 3/2018 | Shelton, IV |
| 9,918,714 B2 | 3/2018 | Gibbons, Jr. |
| 9,918,717 B2 | 3/2018 | Czernik |
| 9,924,941 B2 | 3/2018 | Burbank |
| 9,924,942 B2 | 3/2018 | Swayze et al. |
| 9,936,951 B2 | 4/2018 | Hufnagel et al. |
| 9,936,954 B2 | 4/2018 | Shelton, IV et al. |
| 9,943,311 B2 | 4/2018 | Scirica et al. |
| 9,949,737 B2 | 4/2018 | Zergiebel et al. |
| 9,955,966 B2 | 5/2018 | Zergiebel |
| 9,968,354 B2 | 5/2018 | Shelton, IV et al. |
| 9,980,724 B2 | 5/2018 | Farascioni et al. |
| 9,987,012 B2 | 6/2018 | Shah |
| 9,987,099 B2 | 6/2018 | Chen et al. |
| 9,993,248 B2 | 6/2018 | Shelton, IV et al. |
| 9,993,258 B2 | 6/2018 | Shelton, IV et al. |
| 10,004,497 B2 | 6/2018 | Overmyer et al. |
| 10,004,505 B2 | 6/2018 | Moore et al. |
| 10,034,668 B2 | 7/2018 | Ebner |
| 10,039,532 B2 | 8/2018 | Srinivas et al. |
| 10,039,545 B2 | 8/2018 | Sadowski et al. |
| 10,045,782 B2 | 8/2018 | Murthy Aravalli |
| 10,052,044 B2 | 8/2018 | Shelton, IV et al. |
| 10,058,963 B2 | 8/2018 | Shelton, IV et al. |
| 10,064,622 B2 | 9/2018 | Murthy Aravalli |
| 10,076,325 B2 | 9/2018 | Huang et al. |
| 10,085,750 B2 | 10/2018 | Zergiebel et al. |
| 10,092,290 B2 | 10/2018 | Yigit et al. |
| 10,092,292 B2 | 10/2018 | Boudreaux et al. |
| 10,111,657 B2 | 10/2018 | McCuen |
| 10,111,665 B2 | 10/2018 | Aranyi |
| 10,117,650 B2 | 11/2018 | Nicholas et al. |
| 10,117,654 B2 | 11/2018 | Ingmanson et al. |
| 10,123,796 B2 | 11/2018 | Westling et al. |
| 10,123,798 B2 | 11/2018 | Baxter, III et al. |
| 10,135,242 B2 | 11/2018 | Baber et al. |
| 10,143,474 B2 | 12/2018 | Bucciaglia et al. |
| 10,172,612 B2 | 1/2019 | Frushour |
| 10,172,615 B2 | 1/2019 | Marczyk et al. |
| 10,172,617 B2 | 1/2019 | Shelton, IV et al. |
| 10,175,127 B2 | 1/2019 | Collins et al. |
| 10,180,463 B2 | 1/2019 | Beckman et al. |
| 10,182,816 B2 | 1/2019 | Shelton, IV et al. |
| 10,206,677 B2 | 2/2019 | Harris et al. |
| 10,213,201 B2 | 2/2019 | Shelton, IV et al. |
| 10,219,804 B2 | 3/2019 | Linder et al. |
| 10,226,239 B2 | 3/2019 | Nicholas et al. |
| 10,226,250 B2 | 3/2019 | Beckman et al. |
| 10,226,254 B2 | 3/2019 | Cabrera et al. |
| 10,245,033 B2 | 4/2019 | Overmyer et al. |
| 10,245,038 B2 | 4/2019 | Hopkins et al. |
| 10,251,725 B2 | 4/2019 | Valentine et al. |
| 10,265,065 B2 | 4/2019 | Shelton, IV et al. |
| 10,265,066 B2 | 4/2019 | Measamer et al. |
| 10,265,074 B2 | 4/2019 | Shelton, IV et al. |
| 10,271,840 B2 | 4/2019 | Sapre |
| 10,271,841 B2 | 4/2019 | Overmyer et al. |
| 10,285,694 B2 | 5/2019 | Viola et al. |
| 10,285,698 B2 | 5/2019 | Cappola et al. |
| 10,321,907 B2 | 6/2019 | Shelton, IV et al. |
| 10,327,776 B2 | 6/2019 | Harris et al. |
| 10,335,150 B2 | 7/2019 | Shelton, IV |
| 10,349,939 B2 | 7/2019 | Shelton, IV et al. |
| 10,349,941 B2 | 7/2019 | Marczyk et al. |
| 10,390,823 B2 | 8/2019 | Shelton, IV et al. |
| 10,390,825 B2 | 8/2019 | Shelton, IV et al. |
| 10,390,828 B2 | 8/2019 | Vendely et al. |
| 10,405,857 B2 | 9/2019 | Shelton |
| 10,426,468 B2 | 10/2019 | Contini et al. |
| 10,441,279 B2 | 10/2019 | Shelton, IV et al. |
| 10,456,129 B2 | 10/2019 | Shelton, IV et al. |
| 10,456,130 B2 | 10/2019 | Cheney et al. |
| 10,463,368 B2 | 11/2019 | Kostrzewski |
| 10,470,762 B2 | 11/2019 | Leimbach et al. |
| 10,470,911 B2 | 11/2019 | Thompson et al. |
| 10,478,182 B2 | 11/2019 | Taylor |
| 10,478,183 B2 | 11/2019 | Hess et al. |
| 10,478,187 B2 | 11/2019 | Shelton, IV et al. |
| 10,542,976 B2 | 1/2020 | Calderoni et al. |
| 10,548,504 B2 | 2/2020 | Shelton, IV et al. |
| 10,548,593 B2 | 2/2020 | Shelton, IV et al. |
| 10,548,599 B2 | 2/2020 | Marczyk et al. |
| 10,561,417 B2 | 2/2020 | Zergiebel et al. |
| 10,561,418 B2 | 2/2020 | Richard et al. |
| 10,568,621 B2 | 2/2020 | Shelton, IV et al. |
| 10,588,629 B2 | 3/2020 | Malinouskas et al. |
| 10,595,929 B2 | 3/2020 | Boudreaux et al. |
| 10,603,128 B2 | 3/2020 | Zergiebel et al. |
| 10,617,412 B2 | 4/2020 | Shelton, IV et al. |
| 10,624,634 B2 | 4/2020 | Shelton, IV et al. |
| 10,687,806 B2 | 6/2020 | Shelton, IV et al. |
| 10,695,053 B2 | 6/2020 | Hess et al. |
| 10,779,822 B2 | 9/2020 | Yates et al. |
| 10,792,038 B2 | 10/2020 | Becerra et al. |
| 10,828,030 B2 | 11/2020 | Weir et al. |
| 10,863,984 B2 | 12/2020 | Shelton, IV et al. |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0216055 A1 | 9/2005 | Scirica et al. |
| 2006/0049229 A1 | 3/2006 | Milliman et al. |
| 2006/0151569 A1* | 7/2006 | Ehrenfels ......... A61B 17/07207 |
| | | 227/19 |
| 2006/0180634 A1 | 8/2006 | Shelton et al. |
| 2006/0289602 A1 | 12/2006 | Wales et al. |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0194079 A1 | 8/2007 | Hueil et al. |
| 2007/0194082 A1 | 8/2007 | Morgan et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0110961 A1 | 5/2008 | Voegele et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296346 A1 | 12/2008 | Shelton, IV et al. |

(56) References Cited

U.S. PATENT DOCUMENTS

| 2008/0308602 A1 | 12/2008 | Timm et al. |
| 2008/0308603 A1 | 12/2008 | Shelton et al. |
| 2008/0308608 A1 | 12/2008 | Prommersberger |
| 2009/0001121 A1 | 1/2009 | Hess et al. |
| 2009/0001130 A1 | 1/2009 | Hess et al. |
| 2009/0090763 A1 | 4/2009 | Zemlok et al. |
| 2009/0090766 A1 | 4/2009 | Knodel |
| 2009/0242610 A1 | 10/2009 | Shelton, IV et al. |
| 2009/0255974 A1 | 10/2009 | Viola |
| 2009/0308907 A1 | 12/2009 | Nalagatla et al. |
| 2010/0012703 A1 | 1/2010 | Calabrese et al. |
| 2010/0065604 A1 | 3/2010 | Weng |
| 2010/0069942 A1 | 3/2010 | Shelton, IV |
| 2010/0127041 A1 | 5/2010 | Morgan et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0193566 A1 | 8/2010 | Scheib et al. |
| 2010/0224668 A1 | 9/2010 | Fontayne et al. |
| 2010/0249802 A1 | 9/2010 | May et al. |
| 2010/0252611 A1 | 10/2010 | Ezzat et al. |
| 2011/0006101 A1 | 1/2011 | Hall et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0087276 A1 | 4/2011 | Bedi et al. |
| 2011/0101069 A1 | 5/2011 | Bombard et al. |
| 2011/0147433 A1 | 6/2011 | Shelton, IV et al. |
| 2011/0163146 A1 | 7/2011 | Ortiz et al. |
| 2011/0192882 A1 | 8/2011 | Hess et al. |
| 2011/0278343 A1 | 11/2011 | Knodel et al. |
| 2011/0290856 A1 | 12/2011 | Shelton, IV et al. |
| 2012/0053406 A1 | 3/2012 | Conlon et al. |
| 2012/0061446 A1 | 3/2012 | Knodel et al. |
| 2012/0074200 A1 | 3/2012 | Schmid et al. |
| 2012/0080478 A1 | 4/2012 | Morgan et al. |
| 2012/0080495 A1 | 4/2012 | Holcomb et al. |
| 2012/0080498 A1 | 4/2012 | Shelton, IV et al. |
| 2012/0091183 A1 | 4/2012 | Manoux et al. |
| 2012/0138659 A1 | 6/2012 | Marczyk et al. |
| 2012/0193394 A1 | 8/2012 | Holcomb et al. |
| 2012/0193399 A1 | 8/2012 | Holcomb et al. |
| 2012/0211542 A1 | 8/2012 | Racenet |
| 2012/0228358 A1 | 9/2012 | Zemlok et al. |
| 2012/0234895 A1 | 9/2012 | O'Connor et al. |
| 2012/0234897 A1 | 9/2012 | Shelton, IV et al. |
| 2012/0241504 A1 | 9/2012 | Soltz et al. |
| 2012/0248169 A1 | 10/2012 | Widenhouse et al. |
| 2012/0286022 A1 | 11/2012 | Olson et al. |
| 2012/0298722 A1 | 11/2012 | Hess et al. |
| 2013/0008937 A1 | 1/2013 | Viola |
| 2013/0012983 A1 | 1/2013 | Kleyman |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0041406 A1 | 2/2013 | Bear et al. |
| 2013/0068816 A1 | 3/2013 | Mandakolathur Vasudevan et al. |
| 2013/0068818 A1 | 3/2013 | Kasvikis |
| 2013/0075447 A1 | 3/2013 | Weisenburgh, II et al. |
| 2013/0098970 A1 | 4/2013 | Racenet et al. |
| 2013/0153641 A1 | 6/2013 | Shelton, IV et al. |
| 2013/0175316 A1 | 7/2013 | Thompson et al. |
| 2013/0256380 A1 | 10/2013 | Schmid et al. |
| 2013/0277410 A1 | 10/2013 | Fernandez et al. |
| 2013/0334280 A1 | 12/2013 | Krehel et al. |
| 2014/0014704 A1 | 1/2014 | Onukuri et al. |
| 2014/0014707 A1 | 1/2014 | Onukuri et al. |
| 2014/0048580 A1 | 2/2014 | Merchant et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175150 A1 | 6/2014 | Shelton, IV et al. |
| 2014/0239047 A1 | 8/2014 | Hodgkinson et al. |
| 2014/0246475 A1 | 9/2014 | Hall et al. |
| 2014/0249557 A1* | 9/2014 | Koch, Jr. ......... A61B 17/07207 |
| | | 606/170 |
| 2014/0252064 A1 | 9/2014 | Vozdzierz et al. |
| 2014/0252065 A1* | 9/2014 | Hessler .............. A61B 17/0682 |
| | | 227/176.1 |
| 2014/0263541 A1 | 9/2014 | Leimbach et al. |
| 2014/0263552 A1 | 9/2014 | Hall et al. |
| 2014/0263558 A1 | 9/2014 | Hausen et al. |
| 2014/0284371 A1 | 9/2014 | Morgan et al. |
| 2014/0291379 A1 | 10/2014 | Schellin et al. |
| 2014/0291383 A1 | 10/2014 | Spivey et al. |
| 2014/0367445 A1 | 12/2014 | Ingmanson et al. |
| 2015/0076211 A1 | 3/2015 | Irka et al. |
| 2015/0134076 A1 | 5/2015 | Shelton, IV et al. |
| 2015/0173749 A1 | 6/2015 | Shelton, IV et al. |
| 2015/0173756 A1 | 6/2015 | Baxter, III et al. |
| 2015/0250474 A1 | 9/2015 | Abbott et al. |
| 2015/0272557 A1 | 10/2015 | Overmyer et al. |
| 2015/0297222 A1 | 10/2015 | Huitema et al. |
| 2015/0297225 A1 | 10/2015 | Huitema et al. |
| 2015/0374372 A1 | 12/2015 | Zergiebel et al. |
| 2016/0066909 A1 | 3/2016 | Baber et al. |
| 2016/0166249 A1 | 6/2016 | Knodel |
| 2016/0166253 A1 | 6/2016 | Knodel |
| 2016/0235494 A1 | 8/2016 | Shelton, IV et al. |
| 2016/0249929 A1* | 9/2016 | Cappola ........... A61B 17/07207 |
| | | 227/176.1 |
| 2016/0302791 A1 | 10/2016 | Schmitt |
| 2016/0354176 A1 | 12/2016 | Schmitt |
| 2017/0000483 A1 | 1/2017 | Motai et al. |
| 2017/0112561 A1 | 4/2017 | Motai |
| 2017/0290584 A1 | 10/2017 | Jasemian et al. |
| 2017/0296172 A1 | 10/2017 | Harris et al. |
| 2017/0303924 A1 | 10/2017 | Scheib |
| 2018/0008260 A1 | 1/2018 | Baxter, III et al. |
| 2018/0168637 A1 | 6/2018 | Harris |
| 2018/0168644 A1 | 6/2018 | Shelton, IV et al. |
| 2018/0235610 A1 | 8/2018 | Harris et al. |
| 2018/0325514 A1 | 11/2018 | Harris et al. |
| 2019/0099182 A1 | 4/2019 | Bakos et al. |
| 2019/0150919 A1 | 5/2019 | Williams et al. |
| 2019/0261984 A1 | 8/2019 | Nelson et al. |
| 2019/0298341 A1 | 10/2019 | Shelton, IV et al. |
| 2019/0314016 A1 | 10/2019 | Huitema et al. |
| 2019/0314019 A1 | 10/2019 | Rector et al. |
| 2020/0054323 A1 | 2/2020 | Harris et al. |
| 2020/0113562 A1 | 4/2020 | Schings et al. |
| 2020/0121317 A1 | 4/2020 | Kostrzewski |
| 2020/0237368 A1 | 7/2020 | Bruns et al. |
| 2021/0077102 A1 | 3/2021 | Williams |
| 2021/0177408 A1* | 6/2021 | Schings .............. A61B 17/115 |
| 2022/0079596 A1* | 3/2022 | Huitema ........... A61B 17/0682 |

FOREIGN PATENT DOCUMENTS

| CA | 2884962 A1 | 11/2015 |
| CN | 103190938 A | 7/2013 |
| CN | 104207813 A | 12/2014 |
| CN | 106456159 A | 2/2017 |
| CN | 208096781 U | 11/2018 |
| CN | 209107454 U | 7/2019 |
| CN | 209789913 U | 12/2019 |
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |

(56) References Cited

FOREIGN PATENT DOCUMENTS

| EP | 0324638 A1 | 7/1989 |
|----|------------|--------|
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0541950 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0760230 A1 | 3/1997 |
| EP | 1952769 A2 | 8/2008 |
| EP | 2090253 A2 | 8/2009 |
| EP | 2090254 A1 | 8/2009 |
| EP | 2583630 A2 | 4/2013 |
| EP | 2586382 A2 | 5/2013 |
| EP | 2907456 A1 | 8/2015 |
| EP | 3138509 A1 | 3/2017 |
| EP | 3338660 A1 | 6/2018 |
| FR | 391239 A | 10/1908 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51149985 | 12/1976 |
| JP | 2001087272 | 4/2001 |
| JP | 2013215572 A | 10/2013 |
| SU | 659146 A1 | 4/1979 |
| SU | 728848 A1 | 4/1980 |
| SU | 980703 A1 | 12/1982 |
| SU | 990220 A1 | 1/1983 |
| WO | 2008302247 | 7/1983 |
| WO | 8910094 A1 | 11/1989 |
| WO | 9210976 A1 | 7/1992 |
| WO | 9308754 A1 | 5/1993 |
| WO | 9314706 A1 | 8/1993 |
| WO | 2004032760 A2 | 4/2004 |
| WO | 2009071070 A2 | 6/2009 |
| WO | 2015191887 A1 | 12/2015 |
| WO | 2018161313 A1 | 9/2018 |
| WO | 2019186434 A1 | 10/2019 |
| WO | 2020035762 A1 | 2/2020 |
| WO | 2020163982 A1 | 8/2020 |

OTHER PUBLICATIONS

Office Action for Chinese Patent Application No. 202111118721.9 mailed Apr. 25, 2025, 11 pages.

* cited by examiner

SURGICAL STAPLING DEVICE WITH SAFETY MEMBER

FIELD

This disclosure relates to a surgical stapling device, and, more particularly, to a surgical stapling device that includes a safety member that prevents inadvertent advancement of a firing assembly of the stapling device prior to actuation of the stapling device.

BACKGROUND

Surgical stapling devices that eject staples to join tissue during surgical procedures are well known. These stapling devices are available in a variety of configurations including linear, curved, and circular to perform open and endoscopic surgical procedures. Linear surgical stapling devices for performing open surgical procedures typically include an anvil section, a cartridge receiving section, a staple cartridge, and a firing assembly. The staple cartridge is releasably secured within the cartridge receiving section, and the firing assembly is movable within the cartridge receiving section to eject staples from the staple cartridge. These stapling devices often include a lockout assembly that prevents movement of the firing assembly within the cartridge receiving section when a staple cartridge is removed from the cartridge receiving section of the stapling device. In such devices, the lockout assembly is moved to an unlocked position upon placement of the staple cartridge into the cartridge receiving section of the stapling device.

In certain linear surgical stapling devices for performing open surgical procedures, the staple cartridge is preloaded into the cartridge receiving section prior to packaging and shipping of the stapling device. In such stapling devices, inadvertent movement of the firing assembly can result in unwanted ejection of staples from the staple cartridge prior to use of the stapling device.

A continuing need exists in the art for a device to prevent inadvertent advancement of the firing assembly within the stapling device.

SUMMARY

This disclosure generally relates to a safety member for use with an open, linear stapling device that can be coupled to a staple cartridge of the stapling device to prevent inadvertent advancement of a firing assembly of the stapling device. This disclosure is also directed to a stapling device including a safety member that can be coupled to the staple cartridge of the stapling device to prevent inadvertent advancement of the firing assembly of the stapling device.

Aspects of the disclosure are directed to a stapling device and safety member assembly that includes a stapling device and a safety member. The stapling device includes an anvil section, a cartridge section, a staple cartridge, a firing assembly, and a clamp member. The anvil section has a proximal portion and a distal portion. The proximal portion includes a hand grip and the distal portion includes an anvil plate. The cartridge section includes a channel member that defines a channel that includes a proximal portion and a distal portion. The staple cartridge includes a body that defines a central knife slot, a knife assembly that includes a knife bar having a cutting edge, and an actuation sled. The staple cartridge is releasably received within the distal portion of the channel defined by the channel member of the cartridge section. The firing assembly includes a drive beam that is adapted to couple to the knife assembly when the staple cartridge is received within the distal portion of the channel defined by the channel member of the cartridge section. The clamp member is supported on the cartridge section and is movable from an unclamped position to a clamped position to move the anvil plate into juxtaposed alignment with the staple cartridge. The safety member includes a body that includes a knife stop and an angled stop surface. The body of the safety member is frictionally received within the central knife slot defined by the cartridge body such that the knife stop engages the cutting edge of the knife bar and the angled stop surface is engaged with the actuation sled to prevent movement of the knife assembly and actuation sled within the body of the staple cartridge.

In aspects of the disclosure, the body of the safety member includes transversely extending protrusions and the body of the staple cartridge defines cutouts, and the transversely extending protrusions are received within the cutouts to prevent longitudinal movement of the safety member within the central knife slot of the cartridge body.

In some aspects of the disclosure, the body of the safety member has a proximal portion that includes the knife stop and the angled stop surface.

In certain aspects of the disclosure, the distal portion of the safety member includes a grip that extends from the central knife slot of the body of the staple cartridge when the safety member is received within the central knife slot of the body of the staple cartridge.

In aspects of the disclosure, the grip includes longitudinal ribs.

In some aspects of the disclosure, the distal portion of the safety member includes feet that engage the channel when the safety member is received within the central knife slot of the body of the staple cartridge.

In certain aspects of the disclosure, the body of the safety member includes raised surfaces that are positioned to engage a portion of the body of the staple cartridge defining the central knife slot when the safety member is coupled to the staple cartridge to retain the safety member within the central knife slot.

In aspects of the disclosure, the firing assembly of the stapling device includes a trigger that is coupled to the drive beam and is movable from a retracted position to an advanced position to advance the knife assembly and the actuation sled through the body of the staple cartridge.

In some aspects of the disclosure, the trigger is pivotally coupled to the drive beam and includes a thumb engagement member on each side of the channel of the cartridge section to facilitate actuation of the firing assembly from both sides of the stapling device.

In certain aspects of the disclosure, the stapling device includes a lock member that is supported within the channel of the channel member of the cartridge section.

In aspects of the disclosure, the lock member defines a slot through which the drive beam of the drive assembly extends, and the lock member is movable from a locked position engaged with the drive beam to an unlocked position disengaged from the drive member.

In some aspects of the disclosure, the lock member is movable from the locked position to the unlocked position in response to insertion of the staple cartridge within the distal portion of the channel of the channel member of the cartridge section of the stapling device.

In certain aspects of the disclosure, the drive beam of the firing assembly includes a distal portion that is adapted to couple to the knife assembly when the staple cartridge is inserted within the distal portion of the channel of the channel member of the cartridge section of the stapling device.

In aspects of the disclosure, the actuation sled defines angled cam surfaces and the angled stop surface of the safety member defines an angle that corresponds to an angle defined by the angled cam surfaces.

Aspects of this disclosure are also directed to a safety member for preventing inadvertent advancement of a knife assembly of a stapling device. The safety member has a body that includes a proximal portion and a distal portion. The distal portion includes a knife stop, an angled stop surface, and transverse protrusions. The body is dimensioned to be frictionally received within a central knife slot of a staple cartridge of the stapling device. The knife stop is positioned to engage a cutting edge of a knife assembly of the stapling device. The angled stop surface is positioned to engage an actuation sled of the staple cartridge of the stapling device, and the protrusions are positioned to be received within cutouts in the staple cartridge to prevent longitudinal movement of the safety member in relation to the staple cartridge.

Other aspects, features, and advantages will be apparent from the description, the drawings, and the claims that follow.

BRIEF DESCRIPTION OF THE DRAWINGS

Various aspects of the disclosure are described herein below with reference to the drawings, wherein.

DETAILED DESCRIPTION

Figure 1:
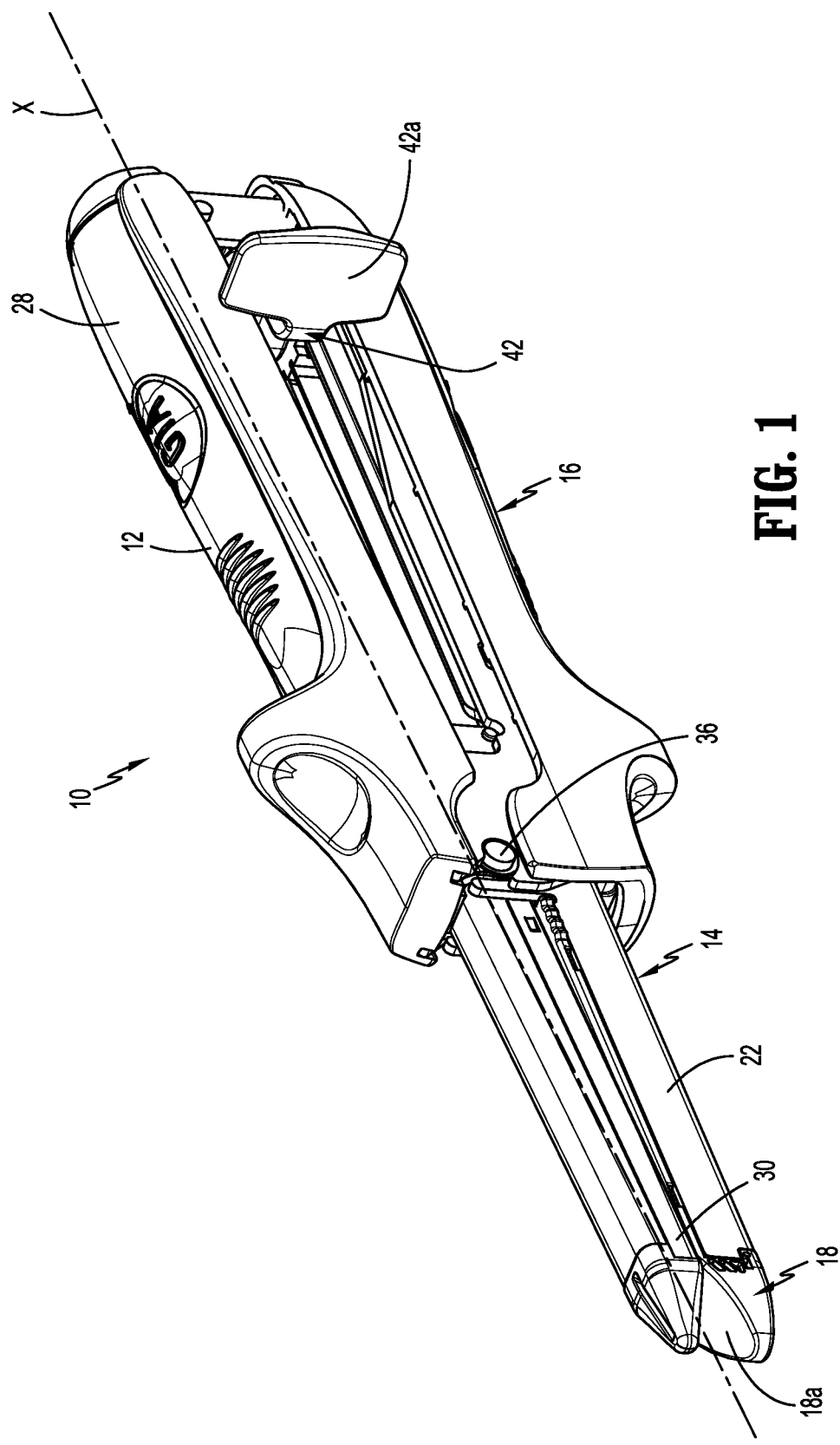
FIG. 1 is a side perspective view of a stapling device including a safety member according to aspects of the disclosure with the stapling device in a clamped position.

The disclosed surgical device will now be described in detail with reference to the drawings in which like reference numerals designate identical or corresponding elements in each of the several views. However, it is to be understood that aspects of the disclosure are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "clinician" is used generally to refer to medical personnel including doctors, nurses, and support personnel. Further, directional terms such as "front", "rear", "upper", "lower", "top", "bottom", and similar terms are used to assist in understanding the description and are not intended to limit the disclosure.

This disclosure is directed to a safety member for use with an open, linear stapling device that includes a body that can be received within a central knife slot of a staple cartridge to prevent inadvertent advancement of a drive assembly of the stapling device. The body of the safety member includes a knife stop, an angled stop surface, and transverse protrusions. The knife stop is positioned on the body to engage a knife assembly of the staple cartridge, and the angled stop surface is positioned to engage an actuation sled of the staple cartridge. The transverse protrusions are positioned to be received within cutouts of the staple cartridge to prevent longitudinal movement of the safety member in relation to the staple cartridge when the safety member is coupled to the staple cartridge.

Figure 1A:
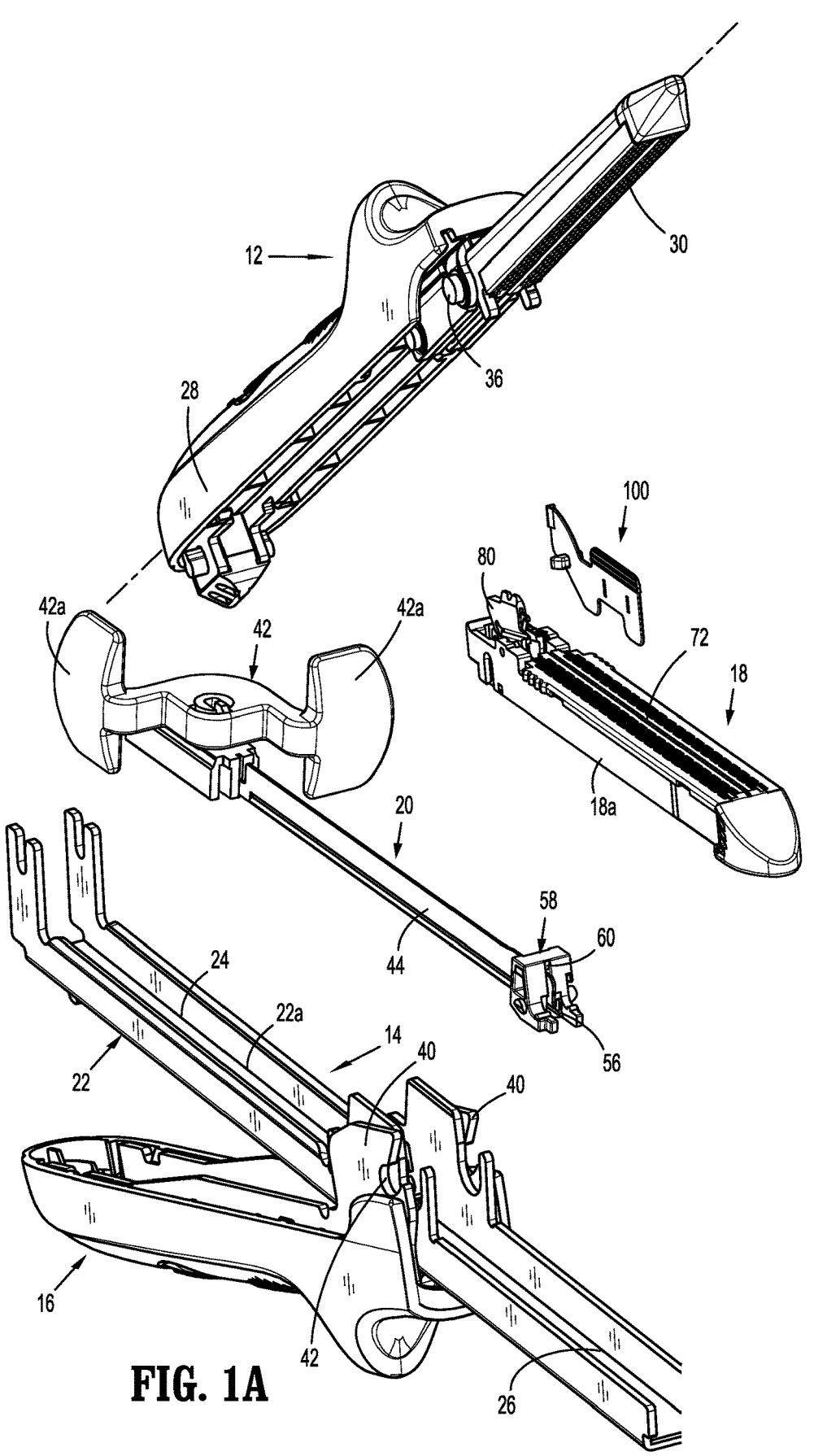
FIG. 1A is an exploded, side perspective view of the stapling device and safety member shown in FIG. 1.
Figure 2:
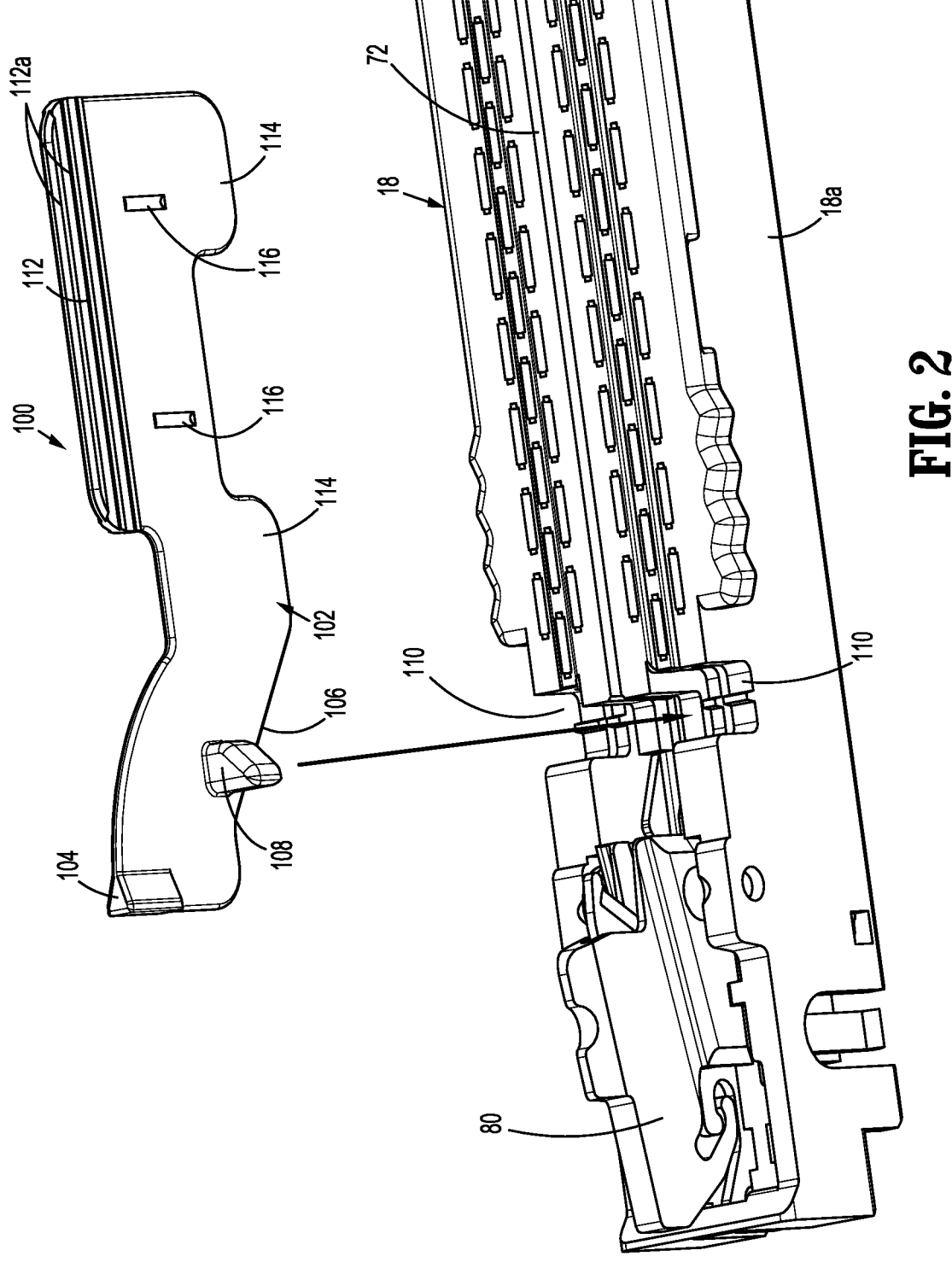
FIG. 2 is a side perspective view of a proximal portion of a staple cartridge of the stapling device shown in FIG. 1A and the safety member with the safety member separated from the staple cartridge.

FIGS. 1 and 1A illustrate a surgical stapling device shown generally as stapling device 10 and a safety member in accordance with the disclosure shown generally as safety member 100. The stapling device 10 defines a longitudinal axis "X" (FIG. 1) and includes an anvil section 12, a cartridge section 14, a clamping lever 16, a staple cartridge 18, and a firing assembly 20 (FIG. 1A). The cartridge section 14 includes a channel member 22 that defines a channel 22a (FIG. 1a) that has a proximal portion 24 and a distal portion 26. The proximal portion 24 of the channel member 22 receives the firing assembly 20. The distal portion 26 of the channel 22a is dimensioned to releasably receive the staple cartridge 18. The anvil section 12 includes an anvil hand grip 28 that is positioned on a proximal portion of the anvil section 12 and an anvil plate 30 that is positioned on a distal portion of the anvil section 12 and faces the cartridge section 14 when the anvil section 12 and the cartridge section 14 are coupled together. The anvil section 12 also includes centrally located protrusions 36.

The clamping lever 16 is pivotally supported on a proximal portion of the cartridge body 14 and is movable between an unclamped position and a clamped position. The clamping lever 16 includes centrally located spaced flanges 40 that define recesses 42. Each of the recesses 42 receives a respective one of the protrusions 36 of the anvil section 12 when the anvil section 12 is coupled to the cartridge section 14. When the clamp lever 16 is pivoted on the cartridge section 14 from the unclamped position to a position adjacent and aligned with the cartridge section 14, the anvil section 12 is moved into juxtaposed alignment with the cartridge section 14 to move the anvil plate 30 into juxtaposed alignment with the staple cartridge 18.

The firing assembly 20 includes a trigger 42 and a drive beam 44. The trigger 42 is rotatably supported on a proximal portion of the drive beam 44 and includes a thumb engagement member 42a positioned on each side of the stapling device 10. The thumb engagement member 42a (FIG. 1) is rotatable between two positions to facilitate actuation of the stapling device 10 from both sides of the stapling device 10. The pivotable trigger 42 is coupled to a proximal portion of the drive beam 44 and is movable longitudinally within the proximal portion 24 of the channel 22a of the channel member 22 to advance the drive beam 44 from a retracted position to an advanced position. The drive beam 44 includes a distal portion that is adapted to engage a knife assembly 50 (FIG. 6) of the staple cartridge 18 when the staple cartridge 18 is received within the distal portion 26 of the channel member 22. In aspects of the disclosure, the distal portion of the drive beam 44 includes a hook-shaped portion 52 (FIG. 1A).

A lock member 58 is supported within a central portion of the channel 22a of the channel member 22. The lock member 58 defines a slot 60 (FIG. 1A) that receives the drive beam 44. The lock member 58 is pivotable between a locked position in which the lock member 58 is engaged with the drive beam 44 and an unlocked position in which the lock member 58 is positioned to allow the drive beam 44 to move through the slot 60. The lock member 58 is pivotable from the locked position to the unlocked position in response to placement of a staple cartridge 18 within the distal portion 26 of the channel 22a of the channel member 22. In aspects of the disclosure, a biasing member (not shown) is engaged with the lock member 58 to urge the lock member 58 to the locked position.

Figures 5, 6:
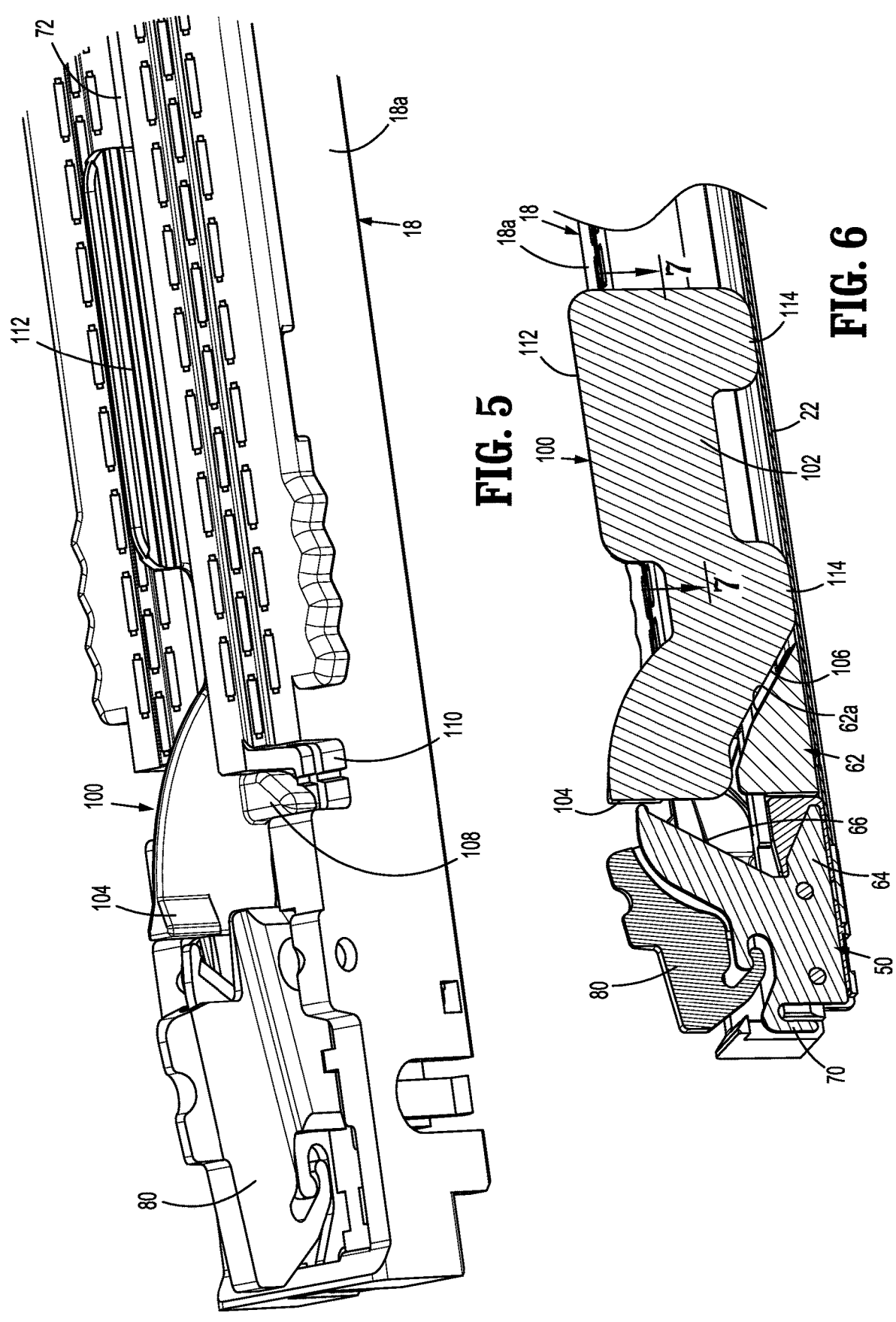
FIG. 5 is an enlarged view of the indicated area of detail shown in FIG. 4.
FIG. 6 is a cross-sectional view taken along section line 6-6 of FIG. 4.
Figure 7:
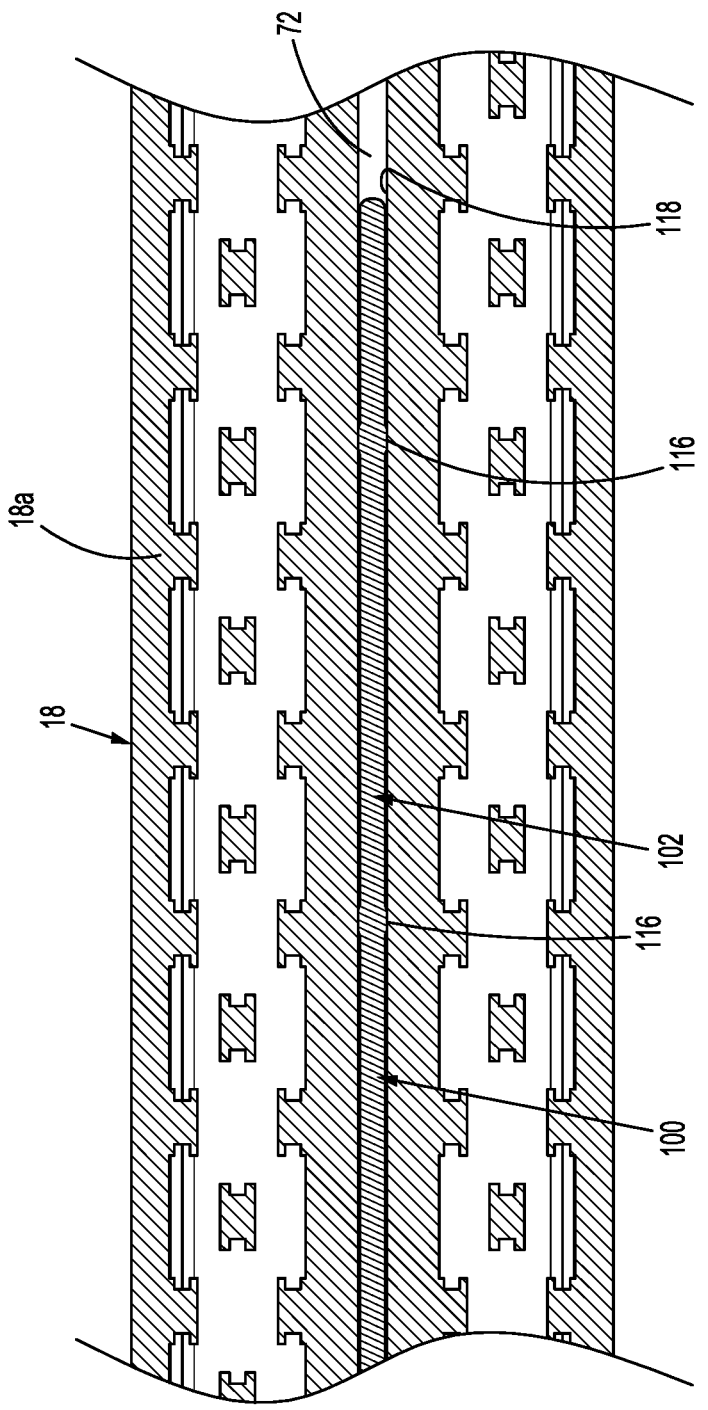
FIG. 7 is a cross-sectional view taken along section line 7-7 of FIG. 6.

The staple cartridge 18 supports the knife assembly 50 (FIG. 6). The knife assembly 50 is in abutting relation to an actuation sled 62 and includes a knife bar 64 that defines a distally facing cutting edge 66 and includes a proximal portion that is adapted to engage the distal portion of the drive beam 44. In aspects of the disclosure, the knife bar 64 includes a proximally extending hook member 70 that engages the hook-shaped portion 52 of the drive beam 44 to couple the knife assembly 50 to the drive beam 44 when the staple cartridge 18 is received within the distal portion 26 of the channel 22a of the channel member 22 of the cartridge section 14. The actuation sled 62 includes angled cam surfaces 62a that engage pushers (not shown) with the body 18a of the staple cartridge 18 to eject staples (not shown) from the staple cartridge 18 when the actuation sled 62 advances through the body 18a of the staple cartridge 18. In aspects of the disclosure, the angled cam surfaces define an acute angle (FIG. 6) with the longitudinal axis "X" of the stapling device 10.

The staple cartridge 18 defines a centrally located knife slot 72 that extends through the staple cartridge 18 from a proximal end of the staple cartridge 18 to a position adjacent a distal end of the staple cartridge 18. The knife bar 64 is movable through the knife slot 72 from a retracted position to an advanced position when the drive bar 44 (FIG. 1A) is advanced from a retracted position to an advanced position to cut tissue clamped between the anvil plate 30 and the staple cartridge 18.

The firing assembly 20 is actuated by advancing the pivotable trigger 42 along the longitudinal axis "X" of the stapling device 10 (FIG. 1) whereby the drive beam 44 advances knife bar 64 distally through a body 18a of the staple cartridge 18. As the knife bar 64 moves distally within the body 18a of the staple cartridge 18, the actuation sled 62 (FIG. 6) is pushed through the body 18a of the staple cartridge 18. The actuation sled 62 cooperates with staple pushers (not shown) within the staple cartridge 18 to eject a plurality of rows of staples from the staple cartridge 18 for engagement and deformation by the anvil plate 30. In aspects of the disclosure, the staple cartridge 18 accommodates two sets of three rows of staples that are delivered through tissue, wherein one set of three rows of staples are positioned on each side of the knife slot 72.

The staple cartridge 18 supports a knife guard 80 that is supported adjacent the knife bar 64. The knife guard 80 is rotatable from an unguarded position in which the cutting edge 66 of the knife bar 64 is exposed to a guarded position in which the cutting edge 66 of the knife bar 64 is covered. For a detailed discussion of the construction and operation of an exemplary surgical stapling instrument including a staple cartridge, reference may be made to commonly assigned U.S. Pat. No. 8,505,801 to Ehrenfels et al.

FIGS. 2-7 illustrate the safety member 100 which includes a body 102 that has a width to be frictionally received within the knife slot 72 of the staple cartridge 18. The body 102 includes a proximal portion that includes a knife stop 104, an angled stop surface 106, and transversely extending protrusions 108. The knife stop 104 is positioned on the proximal end of the body 102 of the safety member 100 to engage the distal end of the knife bar 64 when the safety member 100 is coupled to the staple cartridge 18. The angled stop surface 106 of the body 102 of the safety member 100 is positioned to engage the angled cam surfaces 62a of the actuation sled 62 (FIG. 6) of the staple cartridge 18 to prevent distal movement of the actuation sled 62 within the staple cartridge 18 when the safety member 100 is coupled to the staple cartridge 18. In that respect, the angled stop surface 106 of the safety member 100 can define an angle or angles that correspond to the angle or angles defined by the cam surfaces 62a of the actuation sled 62. The protrusions 108 of the body 102 of the safety member 100 are received within cutouts 110 (FIG. 2) defined in the staple cartridge 18 to axially fix the safety member 100 on the staple cartridge 18.

Figures 3, 4:
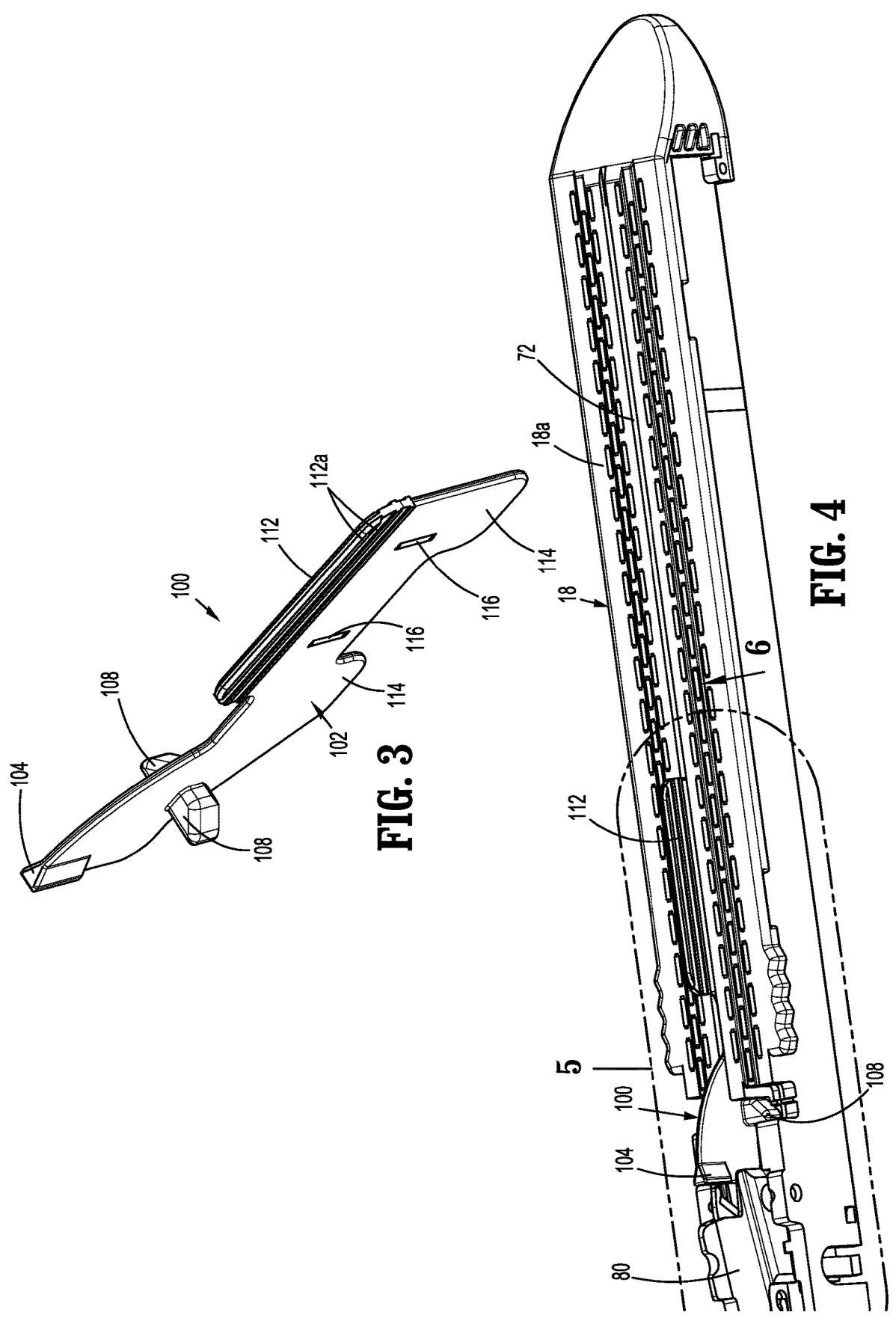
FIG. 3 is a side perspective view of the safety member shown in FIG. 2.
FIG. 4 is a side perspective view from above of the staple cartridge of the stapling device shown in FIG. 1A and the safety member with the safety member secured to the staple cartridge.

In aspects of the disclosure, the body 102 of the safety member 100 includes a distal portion that includes an upper end and a lower end as viewed in FIG. 3. The upper end of the distal portion of the body 102 includes a grip 112 that extends above a top surface of the staple cartridge 18 when the safety member 100 is coupled to the staple cartridge 18 (FIG. 6). In aspects of the disclosure, the grip 112 includes longitudinal ribs 112a (FIG. 2) to improve the grip ability of the grip 112. The lower end of the distal portion of the body 102 includes feet 114 that extend downwardly and engage the channel member 22 when the safety member 100 is coupled to the staple cartridge 18 to prevent further insertion of the safety member 100 into the body 18a of the staple cartridge 18. Although shown to include feet 114, the lower end of the body 102 of the safety member 100 can be continuous along its length such that the entire length of the distal portion of the body 102 of the safety member 100 engages the channel member 22.

In aspects of the disclosure, the body 102 of the distal portion of the safety member 100 includes raised surfaces 116 that engage inner walls 118 (FIG. 7) of the staple cartridge 18 that define the central knife slot 72 to increase the frictional engagement of the safety member 100 with the staple cartridge 18.

FIGS. 4-7 illustrate the safety member 100 coupled to the staple cartridge 18. In order to couple the safety member 100 to the staple cartridge 18, the body 102 of the safety member 100 is inserted into the knife slot 72 defined in the body 18a of the staple cartridge 18. This is accomplished by gripping the grip 112 of the safety member 100 and inserting the feet 114 of the body 102 of the safety member 100 through the knife slot 72 until the feet 114 engage the channel member 22. The safety member 100 is positioned on the staple cartridge 18 such that the protrusions 108 are received within the cutouts 110 defined in the body 18a of the staple cartridge 18. Receipt of the protrusions 102 within the cutouts 110 of the body 18a of the staple cartridge 18 prevents longitudinal movement of the safety member 100 within the knife slot 72. When the protrusions 108 are received in the cutouts 110, the knife stop 104 is engaged with the cutting edge 66 of the knife bar 64 to prevent axial movement of the knife bar 64 within the body 18*a* of the staple cartridge 18. In this position, the angled stop surface 106 of the safety member 100 is engaged with the actuation sled 62 to prevent axial movement of the actuation sled 62 within the body 18*a* of the staple cartridge 18. The raised surfaces 116 (FIG. 7) on the body 102 of the safety member 100 frictionally engage the inner walls 118 of the body 18*a* of the staple cartridge 18 to obstruct removal of the safety member 100 from within the knife slot 72 of the staple cartridge 18.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A stapling device and safety member assembly comprising:
a stapling device extending along a longitudinal axis and including:
an anvil section having a proximal portion and a distal portion, the distal portion including an anvil plate;
a cartridge section including a channel member extending along the longitudinal axis and defining a channel, the channel including a proximal portion and a distal portion;
a staple cartridge, including:
a cartridge body with an upper surface defining a longitudinally-extending central knife slot with a depth defined along a vertical axis, the cartridge body further including side surfaces spaced along a transverse axis and defining cutouts, wherein the vertical axis is orthogonal to the longitudinal axis and the upper surface of the cartridge body, and wherein the transverse axis is orthogonal to the longitudinal axis and the vertical axis;
a knife assembly including a knife bar having a cutting edge; and
an actuation sled movable longitudinally through the cartridge body;
wherein the staple cartridge is releasably received within the distal portion of the channel;
a firing assembly including a drive beam, adapted to couple to the knife assembly when the staple cartridge is received within the distal portion of the channel; and
a clamp member supported on the cartridge section, the clamp member movable from an unclamped position to a clamped position to move the anvil plate into juxtaposed alignment with the staple cartridge; and
a safety member with a body configured for insertion into the central knife slot, the body comprising:
a proximal end defining a knife stop for the knife bar;
an upper end spaced from a lower end along the vertical axis to define a body height, with the upper end defining a grip;

an angled stop surface for engaging the actuation sled; and
side surfaces spaced along the transverse axis to define a body width, with the body height being greater than the body width, and with each side surface having a transversely extending protrusion;
wherein the body width is sized to be frictionally engaged in the central knife slot such that, when the body of the safety member is positioned within the central knife slot:
the body protrudes from the central knife slot such that the grip is positioned vertically above the upper surface of the staple cartridge and a height of the body portion defining the grip has a height greater than the body width;
the knife stop engages the cutting edge of the knife bar,
the angled stop surface engages the actuation sled to prevent movement of the knife assembly and actuation sled within the cartridge body; and
the transversely extending protrusions of the safety member are received within the cutouts of the staple cartridge to prevent longitudinal movement of the safety member within the central knife slot of the cartridge body.

2. The stapling device and safety member assembly of claim 1, wherein the proximal end includes the angled stop surface.

3. The stapling device and safety member assembly of claim 2, wherein the grip includes longitudinal ribs.

4. The stapling device and safety member assembly of claim 2, wherein a distal portion of the safety member includes feet, the feet engaging the channel when the safety member is received within the central knife slot of the cartridge body.

5. The stapling device and safety member assembly of claim 2, wherein the body of the safety member includes raised surfaces that are positioned to engage a portion of the cartridge body defining the central knife slot to retain the safety member within the central knife slot.

6. The stapling device and safety member assembly of claim 1, wherein the firing assembly of the stapling device includes a trigger that is coupled to the drive beam, the trigger being movable from a retracted position to an advanced position to advance the knife assembly and the actuation sled through the cartridge body.

7. The stapling device and safety member assembly of claim 6, wherein the trigger is pivotably coupled to the drive beam and includes a thumb engagement member on each side of the channel of the cartridge section to facilitate actuation of the firing assembly from both sides of the stapling device.

8. The stapling device and safety member assembly of claim 1, wherein the stapling device includes a lock member supported within the channel of the channel member of the cartridge section, the lock member defining a slot through which the drive beam of the firing assembly extends, the lock member movable from a locked position engaged with the drive beam to an unlocked position disengaged from the drive beam.

9. The stapling device and safety member assembly of claim 8, wherein the lock member is movable from the locked position to the unlocked position in response to insertion of the staple cartridge within the distal portion of the channel of the channel member of the cartridge section of the stapling device.

10. The stapling device and safety member assembly of claim 1, wherein the drive beam of the firing assembly includes a distal portion adapted to couple to the knife assembly when the staple cartridge is inserted within the distal portion of the channel of the channel member of the cartridge section of the stapling device.

11. The stapling device and safety member assembly of claim 1, wherein the actuation sled defines angled cam surfaces and the angled stop surface of the safety member defines an angle that corresponds to an angle defined by the angled cam surfaces.

12. A safety member for preventing inadvertent advancement of a knife assembly of a stapling device, the safety member comprising:

a body extending along a longitudinal axis of the stapling device and configured for insertion into a central knife slot of an upper surface of a staple cartridge of the stapling device, the central knife slot defining a depth along a vertical axis orthogonal to the longitudinal axis and the upper surface of the staple cartridge;

wherein the body comprises:

a proximal end defining a knife stop for the knife assembly;

an upper end spaced from a lower end along the vertical axis to define a body height, with the upper end defining a grip;

an angled stop surface for engaging an actuation sled of the staple cartridge; and side surfaces spaced along a transverse axis, orthogonal to the vertical axis and the longitudinal axis, to define a body width, with the body height being greater than the body width, and with each side surface having a transversely extending protrusion;

wherein the body is sized to be frictionally engaged by the central knife slot such that, when the body is positioned within the central knife slot:

the knife stop engages a cutting edge of the knife assembly;

the angled stop surface engages the actuation sled;

the transversely extending protrusions are received within corresponding cutouts in the staple cartridge to prevent longitudinal movement of the safety member in relation to the staple cartridge; and the body protrudes from the central knife slot such that the grip is positioned vertically above the upper surface of the staple cartridge.

13. The safety member of claim 12 wherein the grip includes longitudinal ribs.

14. The safety member of claim 12, wherein the lower end includes feet supporting the safety member within the staple cartridge when the safety member is received within the central knife slot of the staple cartridge.

15. The safety member of claim 12, wherein the body includes raised surfaces that are positioned to engage a portion of the staple cartridge defining the central knife slot to retain the safety member within the central knife slot.

16. The safety member of claim 12, wherein the angled stop surface has an angle that corresponds to an angle of cam surfaces of an actuation sled of the staple cartridge.

17. A stapling device and safety member assembly comprising:

a stapling device extending along a longitudinal axis and including:

an anvil section having a proximal portion and a distal portion;

a cartridge section including a channel member extending along the longitudinal axis and defining a channel, the channel including a proximal portion and a distal portion;

a staple cartridge including:

a cartridge body with an upper surface defining a longitudinally-extending central knife slot, with a depth defined along a vertical axis, the cartridge body further including side surfaces spaced along a transverse axis and defining cutouts, wherein the vertical axis is orthogonal to the longitudinal axis and the upper surface of the cartridge body, and wherein the transverse axis is orthogonal to the longitudinal axis and the vertical axis;

a knife assembly including a knife bar having a cutting edge; and an actuation sled having angled cam surfaces, wherein the staple cartridge is releasably received within the distal portion of the channel; and a firing assembly including a drive beam, the drive beam adapted to couple to the knife assembly when the staple cartridge is received within the distal portion of the channel; and a safety member comprising:

a body that is frictionally received within the central knife slot, the body comprising:

an upper end spaced from a lower end along the vertical axis, the upper end defining a grip including longitudinally extending ribs, and the lower end having one or more feet engaging the channel member when the body is received within the central knife slot;

a proximal end defining a knife stop for the knife bar;

an angled stop surface extending distally from the knife stop and downwards towards the channel, wherein the angled stop surface is positioned to engage angled cam surfaces of the actuation sled to prevent distal movement of the actuation sled; and at least one transversely extending protrusion received within the cutouts defined in the staple cartridge.

18. The stapling device of claim 17, wherein an angle defined by the angled stop surface corresponds to an angle defined by the angled cam surfaces of the actuation sled.

19. The stapling device and safety member assembly of claim 17, wherein the safety member further comprises side surfaces spaced along the transverse axis, at least one of the side surfaces including a raised surface protruding transversely from the body to engage inner walls of the staple cartridge that define the central knife slot to increase the frictional engagement of the safety member with the staple cartridge.

* * * * *